US010317329B2

(12) United States Patent
Cairns et al.

(10) Patent No.: US 10,317,329 B2
(45) Date of Patent: Jun. 11, 2019

(54) EARLY POST-TRANSFECTION ISOLATION OF CELLS (EPIC) FOR BIOLOGICS PRODUCTION

(71) Applicant: Genzyme Corporation, Cambridge, MA (US)

(72) Inventors: Victor R. Cairns, Bridgewater, NJ (US); Christine DeMaria, Bridgewater, NJ (US); Jason Vitko, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/288,050

(22) Filed: Oct. 7, 2016

(65) Prior Publication Data

US 2017/0121734 A1    May 4, 2017

Related U.S. Application Data

(60) Provisional application No. 62/239,515, filed on Oct. 9, 2015.

(51) Int. Cl.

| *C12N 15/85* | (2006.01) |
| *G01N 15/14* | (2006.01) |
| *C12N 15/10* | (2006.01) |
| *C07K 16/00* | (2006.01) |
| *G01N 33/50* | (2006.01) |

(52) U.S. Cl.
CPC ............ *G01N 15/14* (2013.01); *C07K 16/00* (2013.01); *C12N 15/1086* (2013.01); *C12N 15/85* (2013.01); *G01N 33/5044* (2013.01); *C07K 2317/10* (2013.01); *C12N 2510/02* (2013.01); *G01N 2015/149* (2013.01); *G01N 2333/70592* (2013.01)

(58) Field of Classification Search
None
See application file for complete search history.

(56) References Cited

U.S. PATENT DOCUMENTS

| 4,812,405 A | 3/1989 | Lair et al. |
| 4,818,700 A | 4/1989 | Cregg et al. |
| 4,929,555 A | 5/1990 | Cregg et al. |
| 4,937,190 A | 6/1990 | Palmenberg et al. |
| 5,429,746 A | 7/1995 | Shadle et al. |
| 5,648,267 A | 7/1997 | Reff |
| 5,736,383 A | 4/1998 | Raymond |
| 5,888,768 A | 3/1999 | Raymond |
| 5,955,349 A | 9/1999 | Raymond |
| 6,258,559 B1 | 7/2001 | Zamost |
| 6,653,132 B1 | 11/2003 | Keshet et al. |
| 6,833,254 B2 | 12/2004 | Dasgupta et al. |
| 7,776,584 B2 | 8/2010 | Richmond et al. |
| 8,034,612 B2 | 10/2011 | Richmond et al. |
| 8,034,625 B2 | 10/2011 | Richmond et al. |
| 8,293,520 B2 | 10/2012 | Richmond et al. |
| 8,293,525 B2 | 10/2012 | Richmond et al. |
| 8,293,526 B2 | 10/2012 | Richmond et al. |
| 8,293,527 B2 | 10/2012 | Richmond et al. |
| 2004/0082034 A1 | 4/2004 | Lee et al. |
| 2005/0014150 A1 | 1/2005 | Atabekov et al. |
| 2005/0059004 A1 | 3/2005 | Atabekov et al. |
| 2005/0106580 A1* | 5/2005 | Enenkel ............... C12N 9/1205 435/6.16 |
| 2005/0250107 A1 | 11/2005 | Di Colandrea et al. |
| 2006/0141577 A1 | 6/2006 | Otte et al. |
| 2006/0172382 A1 | 8/2006 | Otte et al. |
| 2008/0248468 A1* | 10/2008 | Kubbies ................ C12N 15/111 435/6.11 |
| 2009/0239235 A1 | 9/2009 | Demaria et al. |
| 2010/0159030 A1* | 6/2010 | Kavallaris ............. A61K 31/165 424/649 |

FOREIGN PATENT DOCUMENTS

| AR | 062916 A1 | 12/2008 |
| EP | 1 749 538 A1 | 2/2007 |
| WO | 1991/001374 A1 | 2/1991 |
| WO | 1994/026087 A2 | 11/1994 |
| WO | 1995/027071 A2 | 10/1995 |
| WO | 2001/004306 A1 | 1/2001 |
| WO | 2001/057212 A1 | 8/2001 |

(Continued)

OTHER PUBLICATIONS

Pestova (1998) "A Prokaryotic-like Mode of Cytoplasmic Eukaryotic Ribosome Binding to the Initiation Codon During Internal Translation Initation of Hepatitis C and Classical Swine Fever Virus? RNAs," Genes and Development. 12:67-83.
Pu et al. (1998) "Rapid Establishment of High-Producing Cell Lines Using Discistronic Vectors With Glutamine Synthetase as the Selection Marker," Mol. Biotechnol. 10:17-25.
Rakestraw et al. (2006) "A Flow Cytometric Assay for Screening Improved Heterologous Protein Secretion in Yeast" Biotech. Prog. 22(4):1200-1208.
Ramesh et al. (1996) "High-Titer Bicistronic Retroviral Vectors Employing Foot-and-Mouth Disease Virus Internal Ribosomes Entry Site," Nucleic Acids Research. 24(14):2697-2700.
Rees et al. (1996) "Bicistronic Vector for the Creation of Stable Mammalian Cell Lines that Predisposes all Antibiotic-Resistant Cells to Express Recombinant Protein," Biotechniques. 20:102-110.
Sautter et al. (2005) "Selection of High-Producing CHO Cells Using NPT Selection marker with Reduced Enzyme Activity," Biotech. Bioeng. 89(5):530-538.

(Continued)

*Primary Examiner* — Catherine S Hibbert
(74) *Attorney, Agent, or Firm* — Lathrop Gage LLP; James H. Velema, Esq.

(57) ABSTRACT

Provided herein are methods for selecting a population of cells expressing a target polypeptide. In some aspects, the disclosure provides methods for sorting and selecting populations of transfected host cells based on their early expression of a selectable polypeptide. In certain embodiments, the sorting is performed using fluorescence-activated cell sorting or magnetic-activated cell sorting based on the selectable polypeptide. Such selection methods can be further utilized to generate clonal populations of producer cells, e.g. for large-scale manufacturing of a target polypeptide of interest.

15 Claims, 8 Drawing Sheets

(56) References Cited

FOREIGN PATENT DOCUMENTS

| WO | 2003/099996 A2 | 12/2003 |
| WO | 2004/009823 A1 | 1/2004 |
| WO | 2004/060910 A2 | 7/2004 |
| WO | 2005/000888 A2 | 1/2005 |
| WO | 2005/094886 A1 | 10/2005 |
| WO | 2008/036255 A2 | 3/2008 |
| WO | 2012/001073 A2 | 1/2012 |
| WO | 2014/141037 A1 | 9/2014 |

OTHER PUBLICATIONS

Scharfenberg et al. (1995) "A Reliable Strategy for the Achievement of Cell Lines Growing in Protein-Free Medium," In; Animal Cell Technology: Developments Towards the 21st Century. Eds.: Beuvery et al. pp. 619-623.
Schlatter et al. (2001) "Novel surface tagging technology for selection of complex proliferation-controlled mammalian cell phenotypes," Biotechnology and Bioengineering. 75(5):597-606.
Schlatter et al. (2005) "On the Optimal Ratio of Heavy to Light Chain Genes for Efficient Recombinant Antibody Production by CHO Cells," Biotech Prog. 21:122-133.
Schubert et al. (1999) "Regulation of Virus Release by the Macrophage-Tropic Human Immunodeficiency Virus Type 1 AD8 Isolate Is Redundant and Can Be Controlled by either Vpu or Env," Journal of Virology. 73(2):887-896.
Sen et al. (1990) "Flow Cytometric Study of Hybridoma Cell Culture: Correlation Between Cell Surface Fluorescence and IgG Production Rate," Enzyme Microb. Technol. 12:571-576.
Soriano et al. (2002) "Optimization of Recombinant Protein Expression Level in *Eseherichia coli* by Flow Cytometry and Cell Sorting," Biotechnol. Bioeng. 80(1):93-99.
Tsai et al. (2002) "Evidence for translational regulation of the imprinted Snurf—Snrpn locus in mice," Human Molecular Genetics. 11(14):1659-1668.
Urlaub et al. (1980) "Isolation of Chinese Hamster Cell Mutants Deficient in Dihydrofolate Reductase Activity," Proc. Natl. Acad. Sci. USA. 77(7):4216-4220.
Yoshikawa et al. (2001) "Flow Cytometry: An Improved Method for the Selection of Highly Productive Gene-Amplified CHO Cells Using Flow Cytometry," Biotechnol. Bioeng. 74(5):435-442.
Yuk et al. (2002) "A GFP-Based Screen for Growth-Arrested, Recombinant Protein-Producing Cells," Biotechnol. Bioeng. 79(1):74-82.
Zeyda et al. (1999) "Optimization of Sorting Conditions for the Selection of Stable, High-Producing Mammalian Cell Lines," Biotechnol. Prog. 15:953-957.
Zlokarnik et al. (1998) "Quantitation of Transcription and Clonal Selection of Single Living Cells With 13-Lactamase as Reporter," Science. 279:84-88.
Examination Report corresponding to European Patent Application No. 7838397.3, dated Jul. 22, 2009.
Examination Report corresponding to European Patent Application No. 7838397.3, dated Jul. 7, 2011.
International Preliminary Report on Patentability corresponding to International Patent Application No. PCT/US2007/020180, dated Mar. 24, 2009.
International Search Report with Written Opinion corresponding to International Patent Application No. PCT/US2007/020180, dated May 29, 2008.
International Search Report with Written Opinion corresponding to International Patent Application No. PCT/US2016/055918, dated Jan. 26, 2017.
Invitation to Pay Additional Fees with Annex, A Communication Relating to the Results of the Partial International Search Report, corresponding to International Patent Application No. PCT/US2016/055915, dated Feb. 17, 2017.
Response to Examination Report corresponding to European Patent Application No. 7838397.3, dated Apr. 1, 2010.

Response to Examination Report corresponding to European Patent Application No. 7838397.3, dated Sep. 5, 2011.
Browne et al. (2007) "Selection methods for high-producing mammalian cell lines," Trends in Biotechnology. 25(9):425-232.
Helman et al. (Jun. 13, 2016) "Novel membrane-bound reporter molecule for sorting high producer cells by flow cytometry," Cytometry: Part A. 85(2):162-168.
International Search Report with Written Opinion corresponding to International Patent Application No. PCT/US2007/055915, dated Apr. 6, 2017.
Bailey et al. (2002) "High-Throughput Clonal Selectio of Recombinant CHO Cells Using a Dominant Selectable and Amplifiable Metallothionein-GFP Fusion Protein," Biotech. Bioeng. 80(6):670-676.
Barka et al. (2004) "Production of Cell Lines Secreting TAT Fusion Proteins," J. Histochem. and Cytochem., 52(4):469-477.
Barnes et al. (2003) "Stability of Protein Production from Recombinant Mammalian Cells," Biotech. Bioeng. 81(6):631-639.
Bohm et al. (2004) "Screening for Improved Cell Performance: Selection of Subelones with Altered Production Kinetics or Improved Stability by Cell Sorting," Biotechnol. Bioeng. 88(6):699-706.
Borth et al. (2000) "Efficient Selection of High-Producing Subelones During Gene Amplification of Recombinant Chinese Hamster Ovary Cells by Flow Cytometry and Cell Sorting," Biotechnol. Bioeng. 71(4):266-273.
Brezinsky et al. (2003) "A Simple Method for Enriching Populations of Transfected CHO Cells for Cells of Higher Specific Productivity," J. Immunol. Methods 277:141-155.
Cairns et al. (2011) "Utilization of non-AUG initiation codons in a flow cytometric method for efficient selection of recombinant cell lines," Biotechnol. Bioeng. 108(11):2611-2622.
Carroll et al. (1993) "Translation of equine infectious anemia virus bicistronic tat-rev mRNA requires leaky ribosome scanning of the tat CTG initiation codon," J. Virol. 67(3):1433-1440.
Carroll et al. (2004) "The Selection of High-Producing Cell Lines Using Flow Cytometry and Cell Sorting", Expi. Opin. Biol. Ther. 4(11):1821-1829.
Chen et al. (2004) "Highly Efficient Selection of the Stable Clones Expressing Antibody-IL-2 Fusion Protein by a Dicistronic Expression Vector Containing a Mutant Neo Gene," J. Immunol. Methods. 295:49-56.
Chilov et al. (2004) "Toward construction of a self-sustained clock-like expression system based on the mammalian circadian clock," Biotechnology and Bioengineering. 87(2):234-242.
Choe et al. (2005) "A Dual-Fluorescence Reporter System for High-Throughput Clone Characterization and Selection by Cell Sorting," Nucleic Acids Res. 33(5):1-7.
Clontech Laboratories, Inc. (Sep. 1, 2005) "pIRES Vector Information," Protocol No. PT3266-5. Version No. PR59976.
Condon et al. (2003) "Development of a Chinese Hamster Ovary Cell Line for Recombinant Adenovirus-Mediated Gene Expression," Biotechnol. Prog. 19(1):137-143.
Davies et al. (1992) "The Sequence Context of the Initiation Codon in the Encephalomyocarditis Virus Leader Modulates Efficiency of Internal Translation Initiation," J. Virology 66(4):1924-1932.
Demaria (2012) "Selection of High Expressing Mammalian Cells by Surface Display of Reporters," Ch. 3 In; Methods in Molecular Biology. 801:27-39.
Demaria et al. (2007) "Accelerated Clone Selection for Recombinant CHO Cells Using a FACS-Based High-Throughput Screen," Biotechnology Progress. 23(2):465-472.
Dorn et al. (1990) "Equine infectious anemia virus tat: insights into the structure, function, and evolution of lentivirus trans-activator proteins," Journal of Virology. 64(4):1616-1624.
Drapeau et al. (1994) "Extracellular insulin degrading activity creates instability in a CHO-based batch-refeed continuous process," Cytotechnology. 15:103-109.
Edwards et al. (2004) "Flow Cytometry for High-Throughput, I ligh Content Screening", Curr. Opin. Chem. Biol. 8:392-398.
Fletcher et al. (1992) "New monoclonal antibodies in CD59: use for the analysis of peripheral blood cells from paroxysmal nocturnal haemoglobinuria (PNH) patients and for the quantitation of CD59

(56) References Cited

OTHER PUBLICATIONS on normal and decay accelerating factor (DAF)-deficient erythrocytes," Immunology. 75:507-512.
Fux et al. (2004) "New-generation multicistronic expression platform: pTRIDENT vectors containing size-optimized IRES elements enable homing endonuclease-based cistron swapping into lentiviral expression vectors," Biotechnology and Bioengineering. 86(2):174-187.
Gaines et al. (1999) "pIRES-CD4t, a Dicistronic Expression Vector for MACS- or FACS-Based Selection of Transfected Cells," BioTechniques. 26(4):683-688.
Genbank Database [Online] (Jan. 30, 2011) "*Homo sapiens* CD4 molecule, transcript variant 1, mRNA," Accession No. NM_000616. Accessible on the Internet at URL: http://www.ncbi.nlm.nih.gov/nuccore/NM_000616.4. [Last Accessed Feb. 9, 2011).
Gupta et al. (1988) "ACG, the initiator codon for a Sendai virus protein," Journal of Biological Chemistry. 263(18):8553-8556.
Gurtu et al. (1996) "IRES Bicistronic Expression Vectors for Efficient Creation of Stable Mammalian Cell Lines," Biochem. Biophys. Res. Comm. 229(1):295-298.
Hwang et al. (1998) "Involvement of the 5' proximal coding sequences of hepatitis C virus with internal initiation of viral translation," Biochemical and Biophysical Research Communications. 252(2):455-460.
Jang et al. (1989) "Initiation of Protein Synthesis by Internal Entry of Ribosomes into the 5' Nontranslated Region of Encephalomyocarditis Virus RNA In Vivo," J. Viral. 63(4):1651-1660.
Jang et al. (1998) "A Segment of the 5' Nontranslated Region of Encephalomyocarditis Virus RNA Directs Internal Entry of Ribosomes During In Vitro Translation," J. Virol. 62(8):2636-2643.
Jiang et al. (2006) "Regulation of Recombinant Monoclonal Antibody Production in Chinese Hamster Ovary Cells: A Comparative Study of Gene Copy Number, mRNA Level, and Protein Expression," Biotechnol. Prog. 22:313-318.
Keen et al. (1995) "Development of a serum-free culture medium for the large scale production of recombinant protein from a Chinese hamster ovary cell line," Cytotechnology. 17:153-163.
Kim et al. (1998) "Characterization of Chimeric Antibody Producing CHO Cells in the Course 0 Dihydrofolate Reductase-Mediated Gene Amplification and Their Stability in the Absence 0 Selective Pressure," Biotechnol. Bioeng. 58(1):73-84.
Kim et al. (1998) "Clonal Variability Within Dihydrofolate Reductase-Mediated Gene Amplified Chinese Hamster Ovary Cells: Stability in the Absence of Selective Pressure," Biotech. Bioeng. 60(6):679-688.
Kito et al. (2002) "Construction of Engineered CHO Strains for High-Level Production 0 Recombinant Proteins," Appl. Microbial. Biotechnol. 60:442-448.
Klucher et al. (1997) "A Novel Method to Isolate Cells with Conditional Gene Expression Using Fluorescence Activated Cell Sorting (FACS)," Nucleic Acids Res. 25(23):4858-4860.
Knapp et al. (2003) "Detection of 13-Lactamase Reporter Gene Expression by Flow Cytometry," Cytometry. 51A:68-78.
Koller et al. (2001) "A High-Throughput Alphavirus-Based Expression Cloning System for Mammalian Cells," Nat. Biotechnol. 19:851-855.
Kotarsky et al. (2001) "A Chimeric Reporter Gene Allowing for Clone Selection and High-Throughput Screening of Reporter Cell Lines Expressing G-Protein-Coupled Receptors," Anal. Biochern. 288:209-215.
Kozak (1989) "Context effects and inefficient initiation at non-AUG codons in eukaryotic cell-free translation systems," Mol. Cell. Biol. 9(11):5073-5080.
Kozak (1990) "Downstream secondary structure facilitates recognition of initiator codons by eukaryotic ribosomes," Proc. Natl. Acad. Sci. USA. 87:8301-8305.
Kozak (1991) "An analysis of vertebrate mRNA sequences: intimations of translational control," The Journal of Cell Biology. 115(4):887-903.
Liu et al. (2000) "Generation of Mammalian Cells Stably Expressing Multiple Genes at Predetermined Levels," Analytical Biochemistry. 280:20-28.
Medin et al. (1996) "A Bicistronic Therapeutic Retroviral Vector Enables Sorting of Transduced CD34+ Cells and Corrects the Enzyme Deficiency in Cells from Gaucher Patients," Blood. 87:1754-1762.
Mehdi et al. (1990) "Initiation of Translation at CUG, GUG, and ACG Codones in Mammalian Cells," Gene. 91:173-178.
Meng et al. (2000) "Green Fluorescent Protein as a Second Selectable Marker for Selection of High Producing Clones from Transfected CHO Cells," Gene. 242:201-207.
Mizuguchi et al. (2000) "IRES-Dependent Second Gene Expression is Significantly Lower Thank Cap-Dependent First Gene Expression in a Bicistronic Vector," Mol. Ther. 1(4):376-382.
Mizushima et al. (1990) "pEF-BOS, a powerful mammalian expression vector," Nucleic Acids Research. 18(17):5322.
Moser et al. (2000) "An Update of pTRIDENT Multicistronic Expression Vectors: pTRIDENTS Containing Novel Streptogramin-Responsive Promoters," Biotechnol. Prog. 16:724-735.
Mosser et al. (1997) "Use of a Dicistronic Expression Cassette Encoding the Green Fluorescent Protein for the Screening and Selection of Cells Expressing Inducible Gene Products," BioTechniques. 22:150-161.
Pelletier et al. (1988) "Internal Initiation of Translation of Eukaryotic mRNA Directed by a Sequence Derived from Poliovirus RNA," Nature. 334:320-325.
Mortensen et al. (2009) "Selection of Transfected Mammalian Cells," Ch. 9. Unit 9.5 In; Curr. Protoc. Mol. Biol. pp. 9.5.1-9.5.13.
Sato et al. (Dec. 5, 2014) "A combination of targeted toxin technology and the piggyBac-mediated gene transfer system enables efficient isolation of stable transfectants in nonhuman mammalian cells," Biotechnol. J. 10(1):143-153.
Sato et al. (Mar. 2013) "Targeted Toxin-Based Selectable Drug-Free Enrichment of Mammalian Cells with High Transgene Expression," Biology. 2(1):341-355.
International Search Report with Written Opinion corresponding to International Patent Application No. PCT/US2017/055583, dated Dec. 15, 2017.

\* cited by examiner

EARLY POST-TRANSFECTION ISOLATION OF CELLS (EPIC) FOR BIOLOGICS PRODUCTION

RELATED APPLICATIONS

This application claims the benefit of priority to U.S. Provisional Patent Application No. 62/239,515, filed Oct. 9, 2015. The contents of the aforementioned application are hereby incorporated by reference in their entirety.

BACKGROUND

Methods for selection of producer cell populations and cell clones are imperative for the manufacturing of biologics, such as antibodies and fusion proteins. Such methods generally rely on use of a selection agent, such as methotrexate (MTX) or methionine sulphoximine (MSX), to bias and amplify the production of biologics. Selection agent-based methods may affect the viability or growth rate of selected populations or may have a negative impact on clonal stability. Such drug-based selections can also be time consuming, often requiring multiple rounds of selection to obtain populations which contain clones that are suitable for biologic manufacturing. There remains a need for rapid and reliable methods of generating both large cell populations and clones that produce high titers of biologics with less negative impact to the host cell.

SUMMARY OF THE INVENTION

In some aspects, the disclosure provides methods of selecting a population of cells expressing a target polypeptide. As described herein, methods for selection were developed that relied upon sorting of populations shortly following their transfection. Thus the methods feature the step of isolating a sub-population of transfected cells for early detectable expression of the transfected vector. In certain embodiments, the selection is based on early expression of a selectable polypeptide, which is different from the target polypeptide and detectable on the surface of the cell.

Unexpectedly, the methods described herein were found to be faster than traditional methods which use two rounds of MTX selection to generate a pool, and more productive than traditional MTX amplification, including single-round MTX selection.

The methods described herein are useful, e.g., for the generation of pools of cells for screening of polypeptides of interest (such as in early clinical development and for the generation of high titer clones, which can be utilized to produce a polypeptide of interest both for small and large scale manufacturing.

Accordingly, in some aspects, the disclosure provides a method of producing a population of producer cells expressing a target polypeptide, the method comprising: (a) transfecting host cells with one or more vectors that encode one or more mRNAs, wherein the one or more mRNAs encode a selectable polypeptide and the target polypeptide; (b) isolating from the transfected host cells, within 2 to 15 days after transfection, a sub-population of early-expressing transfected host cells which express the selectable polypeptide; and (c) expanding the sub-population of early-expressing transfected host cells, thereby producing a population of producer cells.

In some embodiments, step (b) is performed in drug-selection-free medium.

In some embodiments, step (c) is performed in drug-selection-free medium.

In some embodiments, step (b) and step (c) are each performed in drug-selection-free medium.

In some embodiments of any one of the methods provided, the method further comprises isolating the target polypeptide from the expanded sub-population.

In some embodiments of any one of the methods provided, the method further comprises isolating one or more single transfected host cells from the expanded sub-population and culturing the one or more single transfected host cells to produce clonal populations of the one or more single transfected host cells.

In some embodiments of any one of the methods provided, at least one of the clonal populations of the one or more single transfected host cells yields a 2- to 30-fold improvement in production of the target polypeptide compared to that of a stable pool of transfected but uncloned host cells obtained at step (c).

In some embodiments of any one of the methods provided, the transfected host cells subject to isolation in step (b) contains $80\text{-}120 \times 10^6$ cells.

In some embodiments of any one of the methods provided, the isolation in step (b) is performed less than six days after transfection. In some embodiments of any one of the methods provided, the isolation in step (b) is performed between two and four days after transfection. In some embodiments of any one of the methods provided, the isolation in step (b) is performed two days after transfection. In some embodiments of any one of the methods provided, the isolation in step (b) is performed three days after transfection.

In some embodiments of any one of the methods provided, the sub-population of transfected host cells contains $0.5\text{-}6.0 \times 10^6$ cells prior to expansion in step (c).

In some embodiments of any one of the methods provided, the expanding in step (c) is for between 4-31 days.

In some embodiments of any one of the methods provided, a first of the one or more vectors encodes the mRNA encoding the target polypeptide, and a second of the one or more vectors encodes the selectable polypeptide.

In some embodiments of any one of the methods provided, the mRNA encoding the target polypeptide and the mRNA encoding the selectable polypeptide are both encoded on one vector.

In some embodiments of any one of the methods provided, a first of the one or more vectors encodes the mRNA encoding the target polypeptide, and a second of the one or more vectors encodes the selectable polypeptide.

In some embodiments of any one of the methods provided, the mRNA encoding the plurality of target polypeptides and the mRNA encoding the plurality of selectable polypeptides are both encoded on one vector.

In some embodiments of any one of the methods provided, the isolation in step (b) employs magnetic-activated cell sorting (MACS), fluorescence-activated cell sorting (FACS), or ClonePix.

In some embodiments of any one of the methods provided, the selectable polypeptide is a FACS selectable polypeptide and the isolation in step (b) employs FACS.

In some embodiments of any one of the methods provided, the target polypeptide and the selectable polypeptide form a fusion polypeptide.

In some embodiments of any one of the methods provided, the mRNA is a multicistronic mRNA. In some embodiments of any one of the methods provided, the multicistronic mRNA comprises a first open reading frame (ORF) that encodes the selectable polypeptide and a second ORF that encodes the target polypeptide, wherein the first ORF is 5' to the second ORF. In some embodiments of any one of the methods provided, the first ORF has a non-AUG start codon. In some embodiments of any one of the methods provided, the second ORF has an AUG start codon. In some embodiments of any one of the methods provided, the non-AUG start codon is a UUG, GUG, or CUG in a Kozak consensus sequence. In some embodiments of any one of the methods provided, the ORF that encodes the selectable polypeptide is devoid of any AUG sequences.

In some embodiments of any one of the methods provided, the selectable polypeptide is CD52 or CD59.

In some embodiments of any one of the methods provided, the target polypeptide is a therapeutic agent. In some embodiments of any one of the methods provided, the target polypeptide is a secreted protein. In some embodiments of any one of the methods provided, the target polypeptide is an antibody or an Fc fusion protein.

In some embodiments of any one of the methods provided, the host cells are CHO cells, HEK293 cells, or HeLa cells.

Other aspects of the disclosure relate to a clonal population of transfected host cells that express a selectable polypeptide and a target polypeptide obtainable by any one of the methods described above or otherwise described herein.

DETAILED DESCRIPTION

Figure 1A:
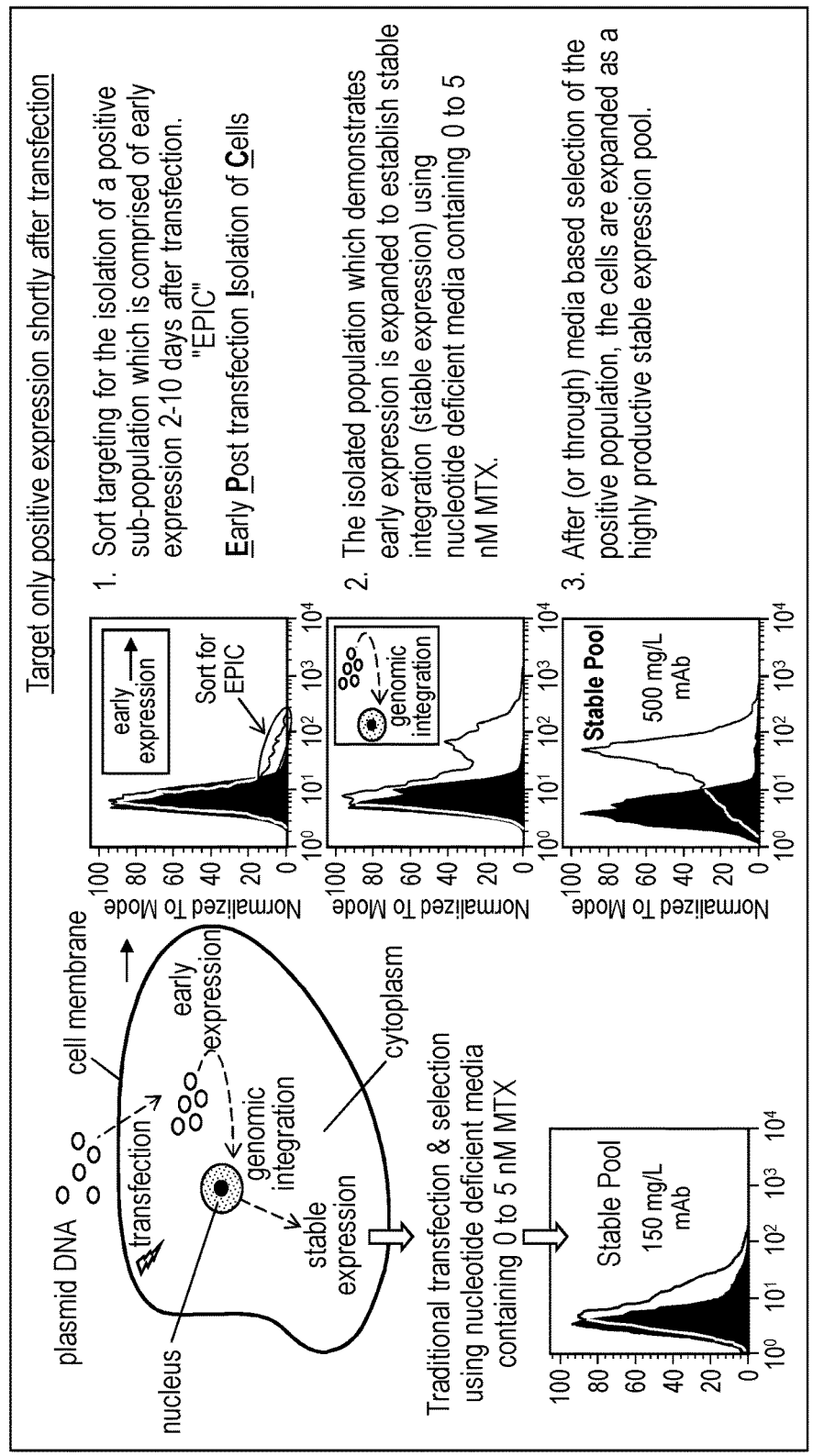
FIG. 1A is a schematic depicting comparison between traditional transfection and selection and EPIC-based transfection and selection. Early expression refers to expression early after transfection, prior to significant genomic integration.

Before the present invention is described, it is to be understood that this invention is not limited to particular methods and experimental conditions disclosed herein; as such methods and conditions may vary. It is also to be understood that the terminology used herein is for the purpose of describing particular embodiments only, and is not intended to be limiting, since the scope of the present invention will be limited only by the appended claims.

Furthermore, the practice of the invention employs, unless otherwise indicated, conventional molecular and cellular biological and immunological techniques within the skill of the art. Such techniques are well known to the skilled worker, and are explained fully in the literature. See, e.g., Ausubel, et al., ed., *Current Protocols in Molecular Biology*, John Wiley & Sons, Inc., NY, N.Y. (1987-2008), including all supplements; M. R. Green and J. Sambrook, *Molecular Cloning: A Laboratory Manual* (Fourth Edition), Cold Spring Harbor Laboratory, Cold Spring Harbor, N.Y. (2012); and Harlow et al., *Antibodies: A Laboratory Manual*, Chapter 14, Cold Spring Harbor Laboratory, Cold Spring Harbor, N.Y. (2013, 2$^{nd}$ edition).

I. Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

As used herein, the term "polynucleotide" intends a polymeric form of nucleotides of any length, examples of which include, but are not limited to, a gene or gene fragment, exons, introns, messenger RNA (mRNA), transfer RNA, ribosomal RNA, ribozymes, complementary DNA (cDNA), recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs.

As used herein, the term "polypeptide" intends a polymeric form of amino acids of any length, examples of which include, but are not limited to, a protein, a protein fragment, a multimeric protein, a fusion protein, an antibody (including fragments thereof), and a peptide.

As used herein, a "selectable polypeptide" is a polypeptide that can be detected, directly or indirectly, by any suitable method including, for example and without limitation, fluorescence-activated cell sorting (FACS), magnetic-activated cell sorting (MACS), ClonePix, and affinity chromatography. In certain embodiments, the selectable polypeptide is expressed on the surface of a cell, i.e., is a cell surface polypeptide. Examples of selectable polypeptides include polypeptides that include an extracellular domain (e.g., CD52 or CD59) that are capable of being bound to or by a detectable binding partner (e.g., a fluorescently-labeled antibody). Other examples of selectable polypeptides include fluorescent proteins such as green fluorescent protein (GFP), red fluorescent protein (RFP), yellow fluorescent protein (YFP), blue fluorescent protein (BFP), and variants thereof including eGFP, Venus, mCherry, mTomato, and the like. In certain embodiments, the selectable polypeptide may be conveniently detected, directly or indirectly, by flow cytometry.

As used herein, "fluorescence-activated cell sorting" or "FACS" refers to a method of separating a population of cells into one or more sub-populations based on the presence, absence, or level of one or more FACS-selectable polypeptides expressed by the cells. FACS relies on optical properties, including fluorescence, of individual cells in order to sort the cells into sub-populations. FACS cell sorters suitable for carrying out a method described herein are well-known in the art and commercially available. Exemplary FACS cell sorters include BD Influx™ (BD Biosciences) and other equivalent cell sorters produced by other commercial vendors such as Sony, Bio-Rad, and Beckman Coulter.

As used herein, a "FACS selectable polypeptide" is a polypeptide that can be detected, directly or indirectly, by flow cytometry. Examples of FACS selectable polypeptides include polypeptides that include an extracellular domain (e.g., CD52 or CD59) that are capable of being bound to a detectable binding partner (e.g., a fluorescently-labeled antibody) for indirect detection of the polypeptide by flow cytometry. Other examples of FACS selectable polypeptides include fluorescent proteins such as green fluorescent protein (GFP), red fluorescent protein (RFP), yellow fluorescent protein (YFP), blue fluorescent protein (BFP), and variants thereof including eGFP, Venus, mCherry, mTomato, and the like, which may be detected directly by flow cytometry.

As used herein, magnetic-activated cell sorting, or "MACS" refers to a method of separating a population of cells into one or more sub-populations based on the presence, absence, or level of one or more MACS-selectable polypeptides expressed by the cells. MACS relies on magnetic susceptibility properties of tagged individual cells in order to sort the cells into sub-populations. MACS cell sorters suitable for carrying out a method described herein are well-known in the art and commercially available. Exemplary MACS cell sorters include MACSQuant® flow cytometer (Miltenyi Biotec).

As used herein, a "MACS selectable polypeptide" is a polypeptide that can be detected, directly or indirectly, by magnetic-activated cell sorting. Examples of MACS selectable polypeptides include polypeptides that include an extracellular domain (e.g., CD52 or CD59) that are capable of being bound to a magnetically susceptible binding partner (e.g., an iron-, nickel-, or cobalt-labeled bead coupled to an antibody) for direct or indirect detection of the polypeptide. In certain embodiments, the selectable polypeptide may be conveniently detected, directly or indirectly, by flow cytometry.

As used herein, "ClonePix" refers to a method of, and device for, separating a population of cells into one or more sub-populations based on the presence, absence, or level of one or more selectable polypeptides expressed by the cells. ClonePix relies on optical properties, including white light and fluorescence detection, of individual cells or colonies of cells in order to sort the cells into sub-populations. ClonePix is described in U.S. Pat. Nos. 7,776,584; 8,034,612; 8,034,625; 8,293,520; 8,293,525; 8,293,526; and 8,293,527, each to Richmond et al., and is commercially available from Molecular Devices (Sunnyvale, Calif.).

As used herein, "target polypeptide" refers to a protein, a protein fragment, a multimeric protein, a fusion protein, an antibody (including fragments thereof), or a peptide that can be produced in host cells and in the aspects exemplified herein, the target polypeptide is selected because of its potential as a therapeutic agent, e.g., an antibody (including a fragment thereof), a Fc fusion protein, a hormone or an enzyme. In some embodiments, the target polypeptide is a secreted protein. However, the methods described herein are not limited for the selection and scale-up of therapeutic polypeptides. For example, diagnostic polypeptides or polypeptides for use in the environment are also contemplated for use as a target polypeptide in a method disclosed herein.

In certain embodiments, the selectable polypeptide is a cell surface polypeptide, and the target polypeptide is a secreted polypeptide.

As used herein, the term "antibody" refers to such assemblies (e.g., intact antibody molecules, antibody fragments, or variants thereof) which have significant known specific immunoreactive activity to an antigen of interest. Antibodies and immunoglobulins comprise light and heavy chains, with or without an interchain covalent linkage between them. Basic immunoglobulin structures in vertebrate systems are relatively well understood.

As used herein, the term "antibody" includes entire antibodies as well as antigen-binding fragments and variants of such antibodies. Antibodies may be of any class, such as IgG, IgA or IgM; and of any subclass, such as IgG1 or IgG4. The antibody can be a polyclonal or a monoclonal antibody, or it can be fragments of the polyclonal or monoclonal antibody. The antibody can be chimeric, humanized, totally human, bi-specific, or bi-functional. Any antigen-binding fragment or variant of an antibody is also contemplated, such as Fab, Fab', F(ab')$_2$, single-chain variable regions (scFv) and variations of the same.

As used herein, an "Fc fusion protein" refers to a protein comprising an immunoglobulin Fc domain that is linked, directly or indirectly, to a polypeptide, such as a protein or peptide. The linked polypeptide can be any proteinaceous molecule of interest, such as a ligand, a receptor, or an antigenic peptide.

As used herein, the term "producer cell" refers to a cell expressing a polypeptide of interest. In certain embodiments, a producer cell is a cell expressing a target polypeptide as disclosed herein. In certain embodiments, a producer cell is a cell expressing both a selectable polypeptide and a target polypeptide as disclosed herein.

In certain embodiments, the term "producer cells" refers to cells that are suitable for production of proteins, e.g., in a small- or large-scale manufacturing method for producing biologics. In some embodiments, producer cells are mammalian or insect cells. Producer cells are further discussed herein.

As used herein, a "population of producer cells" is a population of cells that expresses an enhanced level of one or more polypeptides, e.g., a FACS selectable polypeptide and a target polypeptide that are encoded by the same multicistronic mRNA. In certain embodiments, a "population of producer cells" is a population of cells that expresses an enhanced level of a target polypeptide. In some embodiments, the enhanced level is at least 10-fold, at least 100-fold, at least 1,000-fold, or at least 10,000-fold of the one or more polypeptides in an unselected population. In some embodiments, the enhanced level is at least 10-fold, at least 100-fold, at least 1,000-fold, or at least 10,000-fold of a FACS-selectable polypeptide in an unselected population as detected by flow cytometry (e.g., on a BD Influx™ cell sorter). In some embodiments, the enhanced level is at least 10-fold, at least 100-fold, at least 1,000-fold, or at least 10,000-fold of a MACS-selectable polypeptide in an unselected population as detected by flow cytometry (e.g., on a MACSQuant® flow cytometer (Miltenyi Biotec)). Methods for generating populations of producer cells are described herein.

As used herein, a "population of producer cells" is a population of cells that expresses detectable levels of one or more polypeptides, e.g., a FACS selectable polypeptide and a target polypeptide that are encoded by the same multicistronic mRNA. Methods for generating populations of producer cells are described herein.

As used herein, a "multicistronic mRNA" is an mRNA that contains at least two open reading frames (ORFs) that are capable of encoding two or more polypeptides.

As used herein, a "drug-selection-free medium" is a culture medium that is devoid of a drug (e.g., methotrexate (MTX)) that is used to select a population or sub-populations of cells that express a protein that confers drug resistance (e.g., dihydrofolate reductase) to the population or sub-population.

As used herein, "medium-based selection" is a selection process by which the culture medium is altered to include a selection agent (e.g., MTX) or to exclude a component of medium, which results in selection of a sub-population that is resistant to the selection agent or can survive in the absence of the excluded medium component.

As used herein, "nucleotide-deficient medium" is culture medium that is devoid of or contains low levels (e.g., less than 10 micrograms/mL) of nucleotides having one or more of the nucleobases adenine (A), cytosine (C), guanine (G), thymine (T), hypoxanthine, or thymidine. In some embodiments, nucleotide-deficient medium is medium that is devoid of hypoxanthine and thymidine. Exemplary nucleotide-deficient medium includes CD CHO Medium (Gibco, Life Technologies, Catalogue numbers 10743 (liquid) and 12490 (granulated)).

As used herein, a "viability marker" is a cell characteristic that is indicative of cell viability and is detectable by FACS. Exemplary viability markers include forward scatter, side scatter, propidium iodide stain, or combinations thereof.

As used herein, the term "non-AUG start codon" is intended to include any non-AUG polynucleotide (typically a triplet) that functions as a start site for translation initiation with reduced efficiency relative to that of an AUG start codon. Naturally occurring alternate start codon usage is known in the art and described for example in Kozak (1991) *J. Cell Biol.* 115(4): 887-903; Mehdi et al. (1990) *Gene* 91:173-178; Kozak (1989) *Mol. Cell. Biol.* 9(11): 5073-5080. In general, non-AUG start codons have decreased translation efficiencies compared to that of an AUG; for example, the alternate start codon GUG may have 3-5% translation efficiency compared to that of an AUG (100%). The translation efficiency of a non-AUG start codon can also be affected by its sequence context; for example, an optimal Kozak consensus sequence is reported to have a positive effect on translation initiation at non-AUG start codons (Mehdi et al. (1990) *Gene* 91:173-178; Kozak (1989) *Mol. Cell. Biol.* 9(11): 5073-5080). The complete Kozak DNA consensus sequence is GCCRCCATGG (SEQ ID NO:1), where the start codon ATG (AUG in RNA) is underlined, the A of the ATG start codon is designated as the +1 position, and "R" at position −3 is a purine (A or G). The two most highly conserved positions are a purine, preferably an A, at −3 and a G at +4 (Kozak (1991) *J Cell Biol* 115(4): 887-903). Alternate start codon usage is described for attenuated expression of a selectable marker in U.S. Patent Publication 2006/0172382 and U.S. Patent Publication 2006/0141577, the entire contents of which are incorporated herein by reference. One of skill in the art will recognize that the sequences described herein as DNA will have correlative sequences as RNA molecules, e.g., DNA sequence ATG would correspond to RNA sequence AUG, and vice versa.

As used herein, the term "EPIC" refers to Early Post-transfection Isolation of Cells, as described in more detail herein.

As used herein, the term "FLARE" refers to "FLow Cytometry Attenuated Reporter Expression." FLARE is an expression system utilizing a multicistronic mRNA that contains at least two open reading frames (ORFs), an upstream ORF containing a non-AUG start codon and encoding a FACS selectable polypeptide, and a downstream ORF containing an AUG start codon and encoding a target polypeptide. See U.S. patent application Ser. No. 12/441,806 which is incorporated by reference herein in its entirety.

As used herein, the term "about" shall refer to a range of tolerance of 10% around a stated value. Therefore, when the term "about" is used to modify a stated value, the range indicated will encompass any number within ±0.01%, 0.02%, 0.05%, 0.1%, 0.2%, 0.5%, 1%, 2%, 3%, 4%, 5%, 6%, 7%, 8%, 9%, or 10% of the stated value.

II. Methods for Early Selection of Producer Cells

In some aspects, the disclosure relates to a method of producing a population of producer cells expressing a target polypeptide. In some embodiments, the method comprises:

(a) transfecting host cells with one or more vectors that encode one or more mRNAs, wherein the one or more mRNAs encode a selectable polypeptide and the target polypeptide;

(b) isolating from the transfected host cells, within 2 to 15 days of transfection, a sub-population of early-expressing transfected host cells which express the selectable polypeptide; and (c) expanding the sub-population of transfected host cells, thereby producing a population of producer cells expressing the target polypeptide.

Early-expressing transfected cells can comprise different classes of exogenous DNA, part of which has not integrated into the cells' genomic DNA, and part of which has integrated into the cells' genomic DNA. Both these types of DNA have the potential to lead to expression of the polypeptide or polypeptides they encode.

Host cells are transfected with one or more vectors that encode one or more mRNAs, wherein the one or more mRNAs encode a selectable polypeptide and the target polypeptide. A producer cell can be generated using any cell type suitable for production of a target polypeptide from a multicistronic mRNA. In some embodiments, the host cell is a eukaryotic cell. Examples of suitable eukaryotic cells to produce a target polypeptide include, but are not limited to, a Chinese Hamster Ovary (CHO) cell line, including those designated CHO-DBX11, CHO-DG44, CHO-S, CHO-K1, and the hamster cell line BHK-21; the murine cell lines designated NIH3T3, NS0, C127, the simian cell lines COS, Vero; and the human cell lines HeLa, HEK293 (also called 293), NIH-3T3, U-937 and Hep G2. Additional examples of suitable host cells include yeast cells, insect cells (e.g., *Drosophila* Schnieder S2 cells, Sf9 insect cells (WO 94/26087), BTI-TN-5B1-4 (High Five™) insect cells (Invitrogen)), plant cells, avian cells, and bovine cells. Examples of yeast useful for expression include, but are not limited to *Saccharomyces, Schizosaccharomyces, Hansenula, Candida, Torulopsis, Yarrowia,* and *Pichia*. See e.g., U.S. Pat. Nos. 4,812,405; 4,818,700; 4,929,555; 5,736,383; 5,955,349; 5,888,768 and 6,258,559. Other examples of producer cells can be prokaryotic, including bacterial cells such as *E. coli* (e.g., strain DH5α™) (Invitrogen, Carlsbad, Calif.), PerC6 (Crucell, Leiden, N L), *B. subtilis* and/or other suitable bacteria. The cells can be purchased from a commercial vendor such as the American Type Culture Collection (ATCC, Rockville, Md.) or cultured from an isolate using methods known in the art.

To make a producer cell, recombinant or exogenous polynucleotide(s) can be inserted into the host cell using any suitable transfer technique (e.g., by transfection, transformation, electroporation or transduction). Vectors that encode one or more mRNAs include DNA vectors. Vectors that may be used include plasmids, viruses, phage, transposons, and minichromosomes of which plasmids are a typical embodiment. Generally such vectors further include a signal sequence, origin of replication, one or more marker genes, a promoter and transcription termination sequences operably linked to the gene encoding the multicistronic mRNA so as to facilitate expression. Examples of suitable DNA viral vectors include adenovirus (Ad) and adeno-associated virus (AAV). Adenovirus-based vectors for the delivery of polynucleotides are known in the art and may be obtained commercially or constructed by standard molecular biological methods. Adenoviruses (Ads) are a group of viruses, including over 50 serotypes. See, e.g., International Patent Application No. WO 95/27071. Other viral vectors for use in the present disclosure include vectors derived from vaccinia, herpesvirus (e.g., herpes simplex virus (HSV)), and retroviruses. Gene delivery vehicles also include several non-viral vectors, including DNA/liposome complexes, and targeted viral protein-DNA complexes.

For use in transfection, in certain embodiments circular vectors may be pre-linearized, i.e., linearized prior to introduction into the host cell, for example by restriction at one or more restriction endonuclease sites. Linearization is believed to be necessary for integration into the genome, and this can be effected by pre-linearization or in a random fashion by endonucleases naturally present within the host cell. Pre-linearization has the potential advantage of introducing a degree of control into the site of restriction. Thus, in certain embodiments, circular vectors, including supercoiled circular vectors, may be introduced into the host cell. In certain embodiments in accordance with the instant invention, the one or more vectors are linear at the time of transfection.

Vectors that contain both a promoter and a cloning site into which a polynucleotide can be operatively linked are known in the art and available from commercial vendors. Such vectors are capable of transcribing RNA in vitro or in vivo, and are commercially available from sources such as Agilent Technologies and Promega Corporation. In order to optimize expression and/or in vitro transcription, it may be necessary to remove, add or alter 5' and/or 3' untranslated portions to eliminate extra, potentially inappropriate alternative translation initiation codons or other sequences that may interfere with or reduce expression, either at the level of transcription or translation. Alternatively, consensus ribosome binding sites can be inserted immediately 5' of the start codon to enhance expression.

A promoter can be provided for expression in the producer cell. Promoters can be constitutive or inducible. For example, a promoter can be operably linked to a nucleic acid encoding a multicistronic mRNA such that it directs expression of the encoded polypeptides. A variety of suitable promoters for prokaryotic and eukaryotic hosts are available. Prokaryotic promoters include lac, tac, T3, T7 promoters for *E. coli;* 3-phosphoglycerate kinase or other glycolytic enzymes e.g., enolase, glyceraldehyde 3-phosphate dehydrogenase, hexokinase, pyruvate decarboxylase, phosphofructokinase, glucose 6 phosphate isomerase, 3-phosphoglycerate mutase, and glucokinase. Eukaryotic promoters include inducible yeast promoters such as alcohol dehydrogenase 2, isocytochrome C, acid phosphatase, metallothionein, and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (CMV, in particular, the immediate early gene promoter), retrovirus, hepatitis B virus, actin, Rous sarcoma virus (RSV) promoter, and the early or late Simian virus 40 (SV40) and non-viral promoters such as EF-1 alpha (Mizushima and Nagata (1990) *Nucleic Acids Res.* 18(17):5322). Those of skill in the art will be able to select the appropriate promoter for expressing any given polypeptide in a given host cell.

Where appropriate, e.g., for expression in cells of higher eukaryotes, additional enhancer elements can be included instead of or as well as those found located in the promoters described above. Suitable mammalian enhancer sequences include enhancer elements from globin, elastase, albumin, fetoprotein, metallothionein, and insulin. Alternatively, one may use an enhancer element from a eukaryotic cell virus such as SV40 enhancer, cytomegalovirus early promoter enhancer, polyoma enhancer, baculoviral enhancer or murine IgG2a locus (see, WO 2004/009823). Whilst such enhancers are often located on the vector at a site upstream to the promoter, they can also be located elsewhere, e.g., within the untranslated region or downstream of the polyadenylation signal. The choice and positioning of enhancer may be based upon compatibility with the host cell used for expression.

In addition, the vectors (e.g., expression vectors) may comprise a selectable marker for selection of host cells carrying the vector, and, in the case of a replicable vector, an origin of replication. Genes encoding products which confer antibiotic or drug resistance are common selectable markers and may be used in prokaryotic (e.g., f3-lactamase gene (ampicillin resistance), tet gene (tetracycline resistance) and eukaryotic cells (e.g., neomycin (G418 or geneticin), gpt (mycophenolic acid), ampicillin, or hygromycin B resistance genes). The dihydrofolate reductase (DHFR) gene permits selection with methotrexate or nucleotide-deficient medium in a variety of hosts. Similarly, the glutamine synthetase (GS) gene permits selection with methionine sulphoximine. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals may be operably linked to a polynucleotide encoding the multicistronic mRNA as described herein. Such signals are typically placed 3' of an open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polyadenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host cell specific codon modification.

The producer cells of the disclosure contain a recombinant polynucleotide (e.g., a recombinant cDNA) that encodes a multicistronic mRNA molecule from which the target and selectable polypeptides are separately translated from different ORFs. In some embodiments, the selectable polypeptide is a cell surface polypeptide. In certain embodiments, the producer cells of the disclosure contain a plurality of recombinant polynucleotides, each of which encodes a multicistronic mRNA molecule from which a target polypeptide and a selectable polypeptide are separately translated from different ORFs. Each target polypeptide can thus be associated with a particular selectable polypeptide. In some embodiments, the selectable polypeptide is a cell surface polypeptide.

Examples of cell surface polypeptides include, but are not limited to CD2, CD20, CD52, and CD59. Exemplary, non-limiting, amino acid sequences for CD52 and CD59 cell surface polypeptides are provided below.

```
Amino Acid Sequence for Exemplary Human CD52
polypeptide:
                                      (SEQ ID NO: 2)
LERFLFLLLTISLLVLVQIQTGLSGQNDTSQTSSPSASSNISGGIFLFFV

ANAIIHLFCFS
```

```
Amino Acid Sequence for Exemplary Human CD59
polypeptide (splice acceptor mutant):
                                      (SEQ ID NO: 3)
LGIQGGSVLFGLLLVLAVFCHSGHSLQCYNCPNPTADCKTAVNCSSDFDA

CLITKAGLQVYNNCWKFEHCNFNDVTTRLRENELTYYCCKKDLCNFNEQL

ENGGTSLSEKTVLLLVTPFLAAAWSLHP
```

```
Amino Acid Sequence for Exemplary Mouse CD52
polypeptide:
                                      (SEQ ID NO: 4)
LKSFLLFLTIILLVVIQIQTGSLGQATTAASGTNKNSTSTKKTPLKSGAS

SIIDAGACSFLFFANTLICLFYLS
```

In some embodiments, a first ORF is provided which encodes a selectable polypeptide, such as CD52 or CD59. Exemplary, non-limiting ORF sequences for CD52 and CD59 are provided below.

```
Nucleotide Sequence for Exemplary Human CD52 ORF:
                                      (SEQ ID NO: 6)
ttggagcgcttcctcttcctcctactcaccatcagcctcctcgttttggt acaaatacaaaccggactctccggacaaaacgacaccagccaaaccagca gcccctcagcatccagcaacataagcggaggcattttccttttcttcgtc gccaacgccataatccacctcttctgcttcagttga
```

```
Nucleotide Sequence for Exemplary Human CD59 ORF:
                                      (SEQ ID NO: 7)
ttgggaatccaaggagggtctgtcctgttcggctgctgctcgtcctcgc tgtcttctgccattccggtcatagcctgcagtgctacaactgtcctaacc caactgctgactgcaaaacagccgtcaattgttcatctgattttgacgcg tgtctcattaccaaagctgggttacaagtgtataacaactgttggaagtt tgagcattgcaatttcaacgacgtcacaacccgcttgagggaaaacgagc taacgtactactgctgcaagaaggacctgtgtaactttaacgaacagctt gaaaacggagggacatccttatcagagaaaacagttcttctgctggtgac tccatttctggcagctgcttggagccttcatccctaa
```

```
Nucleotide Sequence for Exemplary Mouse CD52 ORF:
                                      (SEQ ID NO: 8)
TTGAAGAGCTTCCTCCTCTTCCTCACTATCATTCTTCTCGTAGTCATTCA

GATACAAACAGGATCCTTAGGACAAGCCACTACGGCCGCTTCAGGTACTA

ACAAAAACAGCACCTCCACCAAAAAAACCCCCTTAAAGAGCGGGGCCTCA

TCCATCATCGACGCGGGCGCTTGCAGTTTCCTCTTCTTCGCCAATACCCT

TATTTGCCTCTTCTACCTCAGCTAACTGAGTAA
```

As discussed below, each the foregoing exemplary ORFs has been modified to eliminate all internal ATG triplets.

In some embodiments, a second ORF is provided which encodes a target polypeptide, such as an antibody, enzyme, or Fc fusion protein. In some embodiments, separate translation is accomplished by use of a non-AUG start codon for translation initiation of the selectable polypeptide and the use of an AUG start codon for translation initiation of the target polypeptide. In this embodiment, generally the polynucleotide encoding the target polypeptide is located downstream of the polynucleotide encoding the selectable polypeptide. Separate translation can also be achieved using an internal ribosome entry site (IRES). In some embodiments, the IRES element is located upstream of the polynucleotide encoding the target polypeptide and downstream of the polynucleotide encoding the selectable polypeptide. In some embodiments, the IRES element is located upstream of the polynucleotide encoding the selectable polypeptide and downstream of the polynucleotide encoding the target polypeptide.

In some embodiments, a non-AUG start codon is located within the DNA encoding the selectable polypeptide in such a way that translation of the selectable polypeptide is less efficient than translation of the target polypeptide. To achieve decreased translation efficiency, the AUG start codon of the selectable polypeptide may be changed to an alternate non-AUG start codon, examples of which include but are not limited to: CUG, GUG, UUG, AUU, AUA, and ACG.

Thus, when using an alternate non-AUG start codon, expression of a selectable polypeptide can be attenuated relative to that of a co-expressed target polypeptide. In addition to alteration of the start codon, the DNA encoding the selectable polypeptide may be modified at all internal ATG triplets to prevent internal initiation of translation. In some embodiments, the selectable polypeptide has a short amino acid sequence (<200 amino acids) and is encoded by a polynucleotide with few (<10) ATG triplets.

Without wishing to be bound by theory, to initiate translation of the mRNA encoding both the selectable polypeptide and the target polypeptide, ribosomes begin scanning at the 5' cap structure of the mRNA with the majority scanning past the alternate start codon (for example, UUG) and instead initiating translation at the downstream AUG start codon. However, translation initiation can occur at the alternate start codon, albeit with very low frequency, so that a low level of the selectable polypeptide is also expressed.

From the transfected host cells is selected a sub-population of early-expressing transfected host cells which express detectable levels of the selectable polypeptide. During transfection individual host cells take up different amounts of exogenous polynucleotide, e.g., DNA, in an essentially random manner. Some cells will take up many copies of the exogenous polynucleotide, others will take up fewer copies, and some will take up none. The amount of DNA taken up into a given cell affects the fate of the DNA, including its early expression and its integration into the genome.

Following transfection with DNA, at least some of the polynucleotide that has been introduced into the cell is translocated into the nucleus where it is transcribed into mRNA. In the first few days, expression of the introduced DNA may be driven off one or more classes of DNA, some of which has not yet been integrated into the genome of the host cell, and some of which has been integrated into the genome of the host cell. At this point the extent of expression is believed to be principally proportional to the "dose" of DNA introduced into the host cell and its nucleus. The greater the amount of exogenous DNA taken up by the host cell the greater the degree of early expression. However, a small amount of DNA that has been introduced into the host cell, particularly once it is linear, can become integrated into the genome of the host cell. Thus, in the first several days following transfection, there is a competition between degradation and loss of the exogenous DNA on the one hand, and stochastic integration of the exogenous DNA into the genome on the other hand. Integration can include single or multiple copies of introduced DNA. The greater the amount of exogenous DNA taken up by the host cell, the greater the chance (and degree) of its integration. Ultimately, it is the integrated DNA that is responsible for long-term productive expression, i.e., expression after all nonintegrated DNA (e.g., plasmid or episomal DNA) is degraded to the point of being incapable of meaningful expression.

Thus in the first 2 to about 15 days (e.g., 2 days, 3 days, 4 days, 5 days, 6 days, 7 days, 8 days, 9 days, 10 days, 11 days, 12 days, 13 days, 14 days, 15 days) following transfection, there are early-expressing transfected host cells which express detectable amounts of the selectable polypeptide. Particularly in the first 2-6 days, more particularly in the first 2-4 days, and even more particularly in the first 2-3 days, this early expression is believed to be largely, but not necessarily exclusively, driven off exogenous DNA that has not yet been integrated into the genome of the host cell. During this early period following transfection, there may be some degree of integration of exogenous DNA into the host cell genome. Because this early expression depends on the "dose" of DNA taken up by the host cell and its nucleus, and the dose is essentially random among transfected cells, during this early period the transfected host cells include sub-populations of cells expressing different amounts of polypeptide encoded by the exogenous DNA. Also during this early period the sub-populations of cells expressing greater amounts of polypeptide encoded by the exogenous DNA presumably took up greater amounts of exogenous DNA and therefore have a greater chance of incorporating the DNA into their genome.

Accordingly, the term "early-expressing" or "early expression", as used herein, refers to detectable expression in the first 2 to about 15 days (e.g., 2-15 days, 2-14 days, 2-13 days, 2-12 days, 2-11 days, 2-10 days, 2-9 days, 2-8 days, 2-7 days, 2-6 days, 2-5 days, 2-4 days, 2-3 days, 3-15 days, 3-14 days, 3-13 days, 3-12 days, 3-11 days, 3-10 days, 3-9 days, 3-8 days, 3-7 days, 3-6 days, 3-5 days, 3-4 days, 4-15 days, 4-14 days, 4-13 days, 4-12 days, 4-11 days, 4-10 days, 4-9 days, 4-8 days, 4-7 days, 4-6 days, 4-5 days, 5-15 days, 5-14 days, 5-13 days, 5-12 days, 5-11 days, 5-10 days, 5-9 days, 5-8 days, 5-7 days, 5-6 days, 6-15 days, 6-14 days, 6-13 days, 6-12 days, 6-11 days, 6-10 days, 6-9 days, 6-8 days, 6-7 days, 7-15 days, 7-14 days, 7-13 days, 7-12 days, 7-11 days, 7-10 days, 7-9 days, 7-8 days, 8-15 days, 8-14 days, 8-13 days, 8-12 days, 8-11 days, 8-10 days, 8-9 days, 9-15 days, 9-14 days, 9-13 days, 9-12 days, 9-11 days, 9-10 days) following transfection. In certain embodiments, the term "early-expressing" or "early expression" refers to detectable expression in the first 2 to about 10 days following transfection. In certain embodiments, the term "early-expressing" or "early expression" refers to detectable expression in the first 2 to about 6 days following transfection. In certain embodiments, the term "early-expressing" or "early expression" refers to detectable expression in the first 2 to about 5 days following transfection. In certain embodiments, the term "early-expressing" or "early expression" refers to detectable expression in the first 2 to about 4 days following transfection. In certain embodiments, the term "early-expressing" or "early expression" refers to detectable expression in the first 2 to about 3 days following transfection.

Any method known in the art useful for detecting a cell surface marker may be used in connection with the methods of the disclosure. For example, an antibody or other cell surface marker-specific binding agent is contacted directly or indirectly with the transfected host cells under conditions that permit or favor binding of antibody to the selectable polypeptide and thereby select a sub-population of early-expressing transfected host cells. The selection of the antibody or other binding agent is determined by: 1) its ability to selectively bind the selectable polypeptide that is expressed on the host cell; and 2) its ability to be labeled with a detectable label or bind to a detectable label, for example, for use in flow cytometry or FACS.

In an alternate embodiment, a first agent can be a protein or peptide that binds to the selectable polypeptide, which first agent also in turn binds to a second agent that is capable of being detectably labeled (e.g., incorporating a fluorescent, enzymatic, colorimetric, magnetically susceptible, or other detectable label). It is intended, although not always explicitly stated that "indirect" binding to the selectable polypeptide includes the use of any number of intermediate partners. In certain embodiments, "indirect" binding to the selectable polypeptide includes the use of one intermediate partner, e.g., one unlabeled antibody or other binding agent.

In some embodiments, the antibody or other binding agent binds directly to the cell surface marker and comprises a fluorescent label. Suitable fluorescent labels include, but are not limited to, fluorescein isothiocyanate (FITC), rhodamine, tetramethylrhodamine, eosin, phycoerythrin (PE), erythrosin, allophycocyanin (APE), coumarin, methyl-coumarins, pyrene, Malachite green, stilbene, Lucifer Yellow, Cascade Blue, and Texas Red. Other suitable optical dyes are described in the Molecular Probes® Handbook, $11^{th}$ Edition, 2010.

In some embodiments, the fluorescent label is functionalized to facilitate covalent attachment to the antibody or other agent. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to the antibody or other binding agent, the selectable polypeptide, or the second labeling agent.

Attachment of the fluorescent label may be either direct or via a linker to the antibody or other binding agent. In one aspect, the linker is a relatively short coupling moiety that generally is used to attach molecules. In this embodiment, attachment of the first labeling moiety to the candidate agents will be done as is generally appreciated by those in the art, and may include techniques outlined above for the incorporation of fluorescent labels.

Materials and techniques for design and construction of labeled antibodies and other agents for use in cytometry are known in the art and described for example, in Bailey et al. (2002) *Biotechnol. Bioeng.* 80(6); 670-676; Carroll and Al-Rubeai (2004) *Expt. Opin. Biol. Therapy* 4:1821-1829; Yoshikawa et al. (2001) *Biotechnol. Bioeng.* 74:435-442; Meng et al. (2000) *Gene* 242:201-207; Borth et al. (2001) *Biotechnol. Bioeng.* 71 (4):266-273; Zeyda et al. (1999) *Biotechnol. Prog.* 15:953-957; Klucher et al. (1997) *Nucleic Acids Res.* 25(23):4853-4860; and Brezinsky et al. (2003) *J. Imumunol. Methods* 277:141-155.

Suitable binding pairs for use in indirectly linking the label to the agent (which in turn, binds the selectable polypeptide) include, but are not limited to, antigens/antibodies, including digoxigenin/antibody, dinitrophenol (DNP)/anti-DNP, dansyl-X/anti-dansyl, fluorescein/anti-fluorescein, lucifer yellow/anti-lucifer yellow, rhodamine/anti-rhodamine; and biotin/avidin (or biotin/strepavidin). The binding pairs should have high affinities for each other, sufficient to withstand the shear forces during cell sorting or other detection system used in connection with the disclosure.

Thus, in some aspects, first labeling moieties (when second labeling moieties are used), include, but are not limited to, haptens such as biotin. Biotinylation of target molecules is well known, for example, a large number of biotinylation agents are known, including amine-reactive and thiol-reactive agents, for the biotinylation of proteins, nucleic acids, carbohydrates, and carboxylic acids. Similarly, a large number of other haptenylation reagents are also known.

The antibodies used in a method described herein can be produced in cell culture, in phage, or in various animals, including but not limited to cows, mice, rats, hamsters, guinea pigs, rabbits, sheep, goats, horses, cows, camelids, monkeys, chimpanzees, etc., so long as the antibodies retain specificity of binding for the selectable polypeptide. Antibodies can be tested for specificity of binding by comparing binding to appropriate antigen to binding to irrelevant antigen or antigen mixture under a given set of conditions.

In embodiments in which the antibody or other binding agent for the selectable polypeptide is not directly labeled, the antibody or binding agent preferably also contains and retains the ability to bind a secondary agent which is detectable after binding to the cell via the selectable polypeptide.

In some embodiments, when the selectable polypeptide is CD52, the selectable polypeptide may be detected using an anti-CD52 antibody. "Anti-CD52 antibody" refers to an antibody that specifically recognizes and binds CD52. Anti-CD52 antibodies can be generated by methods well known in the art. See for example, *Current Protocols in Molecular Biology* (F. M. Ausubel, et al. eds., 1987 to present versions) and *Antibodies: A Laboratory Manual*, Second edition (Greenfield, ed. 2013). Additionally, several anti-CD52 antibodies are commercially available (e.g., antibodies conjugated to a fluorescent label, such as those sold by the commercial vendors AbCam, SeroTec, and BioLegend).

In some embodiments, when the selectable polypeptide is CD59, the selectable polypeptide may be detected using an anti-CD59 antibody. "Anti-CD59 antibody" refers to an antibody that specifically recognizes and binds CD59. Anti-CD59 antibodies can be generated by methods well known in the art. Additionally, several anti-CD59 antibodies are commercially available (e.g., antibodies conjugated to a fluorescent label, such as those sold by the commercial vendors AbCam, SeroTec, and BioLegend).

In a particular embodiment, when the selectable polypeptide is CD20, the FACS selectable polypeptide may be detected using an anti-CD20 antibody. "Anti-CD20 antibody" refers to an antibody that specifically recognizes and binds CD20. Anti-CD20 antibodies can be generated by methods well known in the art. Additionally, several anti-CD20 antibodies are commercially available from vendors such as BD Pharmingen; Beckman Coulter, Inc. (Fullerton, Calif., numerous clones including Catalog No. 6604106 Clone H299 (B1); Isotype IgG2a and Catalog No. IM1565 Clone L26, Isotype IgG2a); Invitrogen (Carlsbad, Calif., Clone: BH-20, Isotype: IgG2a and Clone: B-H20, Isotype: IgG2a); BioLegend (San Diego, Calif., Catalog. No. 302301, Clone: 21-7, Isotype: IgG2b, κ); EMD Biosciences, Inc., CALBIOCHEM® Brand (San Diego, Calif., Catalog No. 217670 Clone 2H7, Isotype: IgG2b); and Anaspec (San Jose, Calif., Catalog No. 29587).

For use in MACS, where there is a more limited number of antigen-specific magnetic beads, a labeled or unlabeled primary antibody or other binding agent (e.g., Fc fusion protein) can be used to bind to the selectable polypeptide, followed by binding by, for example, an isotype-specific magnetic bead. For example, Miltenyi Biotec sells CD20 microbeads and anti-mouse IgG microbeads, but neither CD52 nor CD59 microbeads; anti-mouse IgG microbeads could be used to label primary mouse IgG anti-human CD52 or mouse IgG anti-human CD59.

In an exemplary, non-limiting method, a population of transfected host cells as described herein is contacted with an agent that recognizes and directly or indirectly binds the selectable polypeptide, if present, on the surface of the cells. The contacting is performed under conditions that favor or are suitable for specific binding (directly or indirectly) of the agent or antibody with the selectable polypeptide. The cells that are bound to the agent or antibody are then selected for using a suitable method such as FACS (e.g., by gating for cells that express the FACS-selectable polypeptide at a high level such as a level that is at least 80% of the level of the population) and used to select a sub-population of early-expressing transfected host cells. Alternatively, the cells that are bound to the agent or antibody are then selected for using a suitable method such as MACS (e.g., by gating for cells that express the MACS-selectable polypeptide at a high level such as a level that is at least 80% of the level of the population) and used to select a sub-population of early-expressing transfected host cells.

The selected sub-population of early-expressing transfected host cells is then grown under conditions that result in expansion of the sub-population to produce a population of producer cells expressing the target polypeptide.

In certain embodiments, the step of isolating from the transfected host cells, within 2 to 15 days of transfection, a sub-population of early-expressing transfected host cells which express the selectable polypeptide is performed in drug-selection-free medium. For example, in certain embodiments, the step of isolating from the transfected host cells, within 2 to 15 days of transfection, a sub-population of early-expressing transfected host cells which express the selectable polypeptide is performed in 0 nM MTX (i.e., MTX-free) medium.

In certain embodiments, the step of expanding the selected sub-population of transfected host cells is performed in drug-selection-free medium. For example, in certain embodiments, the step of expanding the selected sub-population of transfected host cells is performed in 0 nM MTX (i.e., MTX-free) medium.

In certain embodiments, both the step of (b) isolating from the transfected host cells, within 2 to 15 days of transfection, a sub-population of early-expressing transfected host cells which express the selectable polypeptide, and the step of (c) expanding the isolated sub-population of transfected host cells are performed in drug-selection-free medium. For example, in certain embodiments, both the step of (b) isolating from the transfected host cells, within 2 to 15 days of transfection, a sub-population of early-expressing transfected host cells which express the selectable polypeptide, and the step of (c) expanding the isolated sub-population of transfected host cells are performed in 0 nM MTX (i.e., MTX-free) medium.

Cells, including producer cells, may be cultured in spinner flasks, shake flasks, roller bottles, wave reactors (e.g., System 1000 from wavebiotech.com) or hollow fiber systems, or for large scale production, stirred tank reactors or bag reactors (e.g., Wave Biotech, Somerset, N.J. USA) are used particularly for suspension cultures. Stirred tank reactors can be adapted for aeration using e.g., spargers, baffles or low shear impellers. For bubble columns and airlift reactors, direct aeration with air or oxygen bubbles may be used. Where the host cells are cultured in a serum-free culture medium, the medium can be supplemented with a cell protective agent such as poloxamer 188 (Pluronic® F-68) to help prevent cell damage as a result of the aeration process.

Depending on the host cell characteristics, microcarriers may be used as growth substrates for anchorage-dependent cell lines, or the cells may be adapted to suspension culture. The culturing of host cells, particularly vertebrate host cells, may utilize a variety of operational modes such as batch, fed-batch, repeated batch processing (see, Drapeau et al. (1994) *Cytotechnology* 15:103-109), extended batch process or perfusion culture. Although recombinantly transformed producer cells may be cultured in serum-containing media such media comprising fetal calf serum (FCS), in some embodiments, such host cells are cultured in serum-free media such as disclosed in Keen et al. (1995) *Cytotechnology* 17:153-163, or commercially available media such as ProCHO-CDM or UltraCHO™ (Cambrex, N.J., USA), supplemented where necessary with an energy source such as glucose and synthetic growth factors such as recombinant insulin. The serum-free culturing of host cells may require that those cells are adapted to grow in serum-free conditions. One adaptation approach is to culture such host cells in serum containing media and repeatedly exchange 80% of the culture medium for the serum-free media so that the host cells adapt to serum-free conditions (see, e.g., Scharfenberg, K. et al. (1995) In: *Animal Cell Technology: Developments Towards the 21st Century* (Beuvery, E. C. et al., eds), pp. 619-623, Kluwer Academic publishers).

In certain embodiments, the method further comprises isolating the target polypeptide from the population of producer cells. The target polypeptide can be isolated using any method known in the art and may be further purified, e.g., according to Current Good Manufacturing Practice (CGMP) for recombinant proteins and antibodies, to a purity level of at least 90%, at least 95%, at least 96%, at least 97%, at least 98%, at least 99%, at least 99.5%, or more. A target polypeptide according to the described embodiments may be secreted into the medium and recovered and purified therefrom using any of a variety of techniques to provide a degree of purification suitable for the intended use. For example, the use of a target polypeptide (e.g., an antibody or Fc-fusion protein) for the treatment of human subjects typically mandates at least 95% purity as determined by reducing SDS-PAGE, more typically 98% or 99% purity, when compared to the culture media comprising the target polypeptide. In the first instance, cell debris from the culture media can be removed using centrifugation followed by a clarification step of the supernatant using e.g., microfiltration, ultrafiltration and/or depth filtration. Alternatively, a target polypeptide can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC) (see, U.S. Pat. No. 5,429, 746) are available. In one embodiment, a target polypeptide such as an antibody or Fc-fusion protein, following various clarification steps, is captured using Protein A or G affinity chromatography followed by further chromatography steps such as ion exchange and/or HA chromatography, anion or cation exchange, size exclusion chromatography and ammonium sulphate precipitation. Various virus removal steps may also be employed (e.g., nanofiltration using, e.g., a DV-20 filter). Following these various steps, a purified preparation comprising at least 10 mg/mL or greater, e.g., 100 mg/mL or greater of the target polypeptide described herein is provided.

In certain embodiments the methods of the invention further include the step of isolating one or more single transfected host cells from the expanded sub-population and culturing the one or more single transfected host cells to produce clonal populations of the one or more single transfected host cells. In certain embodiments the methods of the invention further include the step of isolating one or more single transfected host cells from the expanded sub-population and culturing the one or more single transfected host cells to produce one or more clonal populations of producer cells expressing the target polypeptide. Preparation of a clonal population can be performed by any method known in the art. For example, in one embodiment, the selected cells may be plated into 96-well (or other size) plates at a density of one cell per well and permitted to grow for a period of time (e.g., typically 7-28 days) which permits the single cell to grow into a multi-cell colony of daughter cells (i.e., a clonal population). The method may next comprise analyzing one or more of the clonal populations by detecting the level of the selectable polypeptide and/or target polypeptide expression on said clonal population and selecting one or more clonal populations with a high expression level of the selectable polypeptide and/or target polypeptide, thereby selecting one or more clonal populations stably expressing the target polypeptide. In certain embodiments, the clonal population is cultured for 7-28 days after plating at a single cell density before the clonal populations are analyzed. The method may further include contacting the clonal population with a detectable antibody or other binding agent that recognizes and directly or indirectly binds the selectable polypeptide, if present, on the surface of the clonal cell under conditions that permit or favor binding of the antibody or other binding agent with the selectable polypeptide; and selecting or detecting one or more cells that are directly or indirectly bound to the antibody or other binding agent. These cells so selected also can be isolated and cultured. The method may further include analyzing target polypeptide expression of the one or more clones, e.g., using protein A screening (such as when the target polypeptide is an antibody or Fc-fusion protein), Western blot, SDS polyacrylamide gel electrophoresis (PAGE) with Coomassie Blue or silver stain, or an enzyme activity assay.

In certain embodiments, the sub-population of transfected host cells subject to isolation in step (b) comprises at least $80\text{-}120\times10^6$ cells. For example, in certain embodiments, the sub-population of transfected host cells subject to isolation in step (b) comprises at least about $80\times10^6$ cells; in certain embodiments, the sub-population of transfected host cells subject to isolation in step (b) comprises at least about $90\times10^6$ cells; in certain embodiments, the sub-population of transfected host cells subject to isolation in step (b) comprises at least about $100\times10^6$ cells; in certain embodiments, the sub-population of transfected host cells subject to isolation in step (b) comprises at least about $110\times10^6$ cells; and in certain embodiments, the sub-population of transfected host cells subject to isolation in step (b) comprises at least about $120\times10^6$ cells. For example, in certain embodiments, the sub-population of transfected host cells subject to isolation in step (b) comprises about $80\times10^6$ to about $800\times10^6$ cells, about $100\times10^6$ to about $800\times10^6$ cells, about $200\times10^6$ to about $800\times10^6$ cells, about $300\times10^6$ to about $800\times10^6$ cells, about $400\times10^6$ to about $800\times10^6$ cells, about $500\times10^6$ to about $800\times10^6$ cells, about $80\times10^6$ to about $600\times10^6$ cells, about $100\times10^6$ to about $600\times10^6$ cells, about $200\times10^6$ to about $600\times10^6$ cells, about $300\times10^6$ to about $600\times10^6$ cells, about $400\times10^6$ to about $600\times10^6$ cells, about $500\times10^6$ to about $600\times10^6$ cells, about $80\times10^6$ to about $500\times10^6$ cells, about $100\times10^6$ to about $500\times10^6$ cells, about $200\times10^6$ to about $500\times10^6$ cells, about $300\times10^6$ to about $500\times10^6$ cells, about $400\times10^6$ to about $500\times10^6$ cells, about $80\times10^6$ to about $400\times10^6$ cells, about $100\times10^6$ to about $400\times10^6$ cells, about $200\times10^6$ to about $400\times10^6$ cells, about $300\times10^6$ to about $400\times10^6$ cells, about $80\times10^6$ to about $300\times10^6$ cells, about $100\times10^6$ to about $300\times10^6$ cells, about $200\times10^6$ to about $300\times10^6$ cells, about $80\times10^6$ to about $250\times10^6$ cells, about $100\times10^6$ to about $250\times10^6$ cells, about $200\times10^6$ to about $250\times10^6$ cells, about $80\times10^6$ to about $200\times10^6$ cells, or about $100\times10^6$ to about $200\times10^6$ cells.

In certain embodiments, the isolation in step (b) is performed less than 6 days after transfection. For example, in certain embodiments, the isolation in step (b) is performed between two and four days after transfection. In certain embodiments, the isolation in step (b) is performed two days after transfection. In certain embodiments, the isolation in step (b) is performed three days after transfection.

In certain embodiments, the sub-population of transfected host cells comprises about $0.5\text{-}6.0\times10^6$ cells prior to expansion in step (c). For example, in certain embodiments, the sub-population of transfected host cells comprises about $0.5\times10^6$ cells, about $1.0\times10^6$ cells, about $2.0\times10^6$ cells, about $3.0\times10^6$ cells, about $4.0\times10^6$ cells, about $5.0\times10^6$ cells, or about $6.0\times10^6$ cells prior to expansion in step (c). For example, in certain embodiments, the sub-population of transfected host cells comprises about $0.5\times10^6$ to about $1.0\times10^6$ cells, about $0.5\times10^6$ to about $2.0\times10^6$ cells, about $0.5\times10^6$ to about $3.0\times10^6$ cells, about $0.5\times10^6$ to about $4.0\times10^6$ cells, about $0.5\times10^6$ to about $5.0\times10^6$ cells, about $0.5\times10^6$ to about $6.0\times10^6$ cells, about $1.0\times10^6$ to about $2.0\times10^6$ cells, about $1.0\times10^6$ to about $3.0\times10^6$ cells, about $1.0\times10^6$ to about $4.0\times10^6$ cells, about $1.0\times10^6$ to about $5.0\times10^6$ cells, about $1.0\times10^6$ to about $6.0\times10^6$ cells, about $2.0\times10^6$ to about $3.0\times10^6$ cells, about $2.0\times10^6$ to about $4.0\times10^6$ cells, about $2.0\times10^6$ to about $5.0\times10^6$ cells, about $2.0\times10^6$ to about $6.0\times10^6$ cells, about $3.0\times10^6$ to about $4.0\times10^6$ cells, about $3.0\times10^6$ to about $5.0\times10^6$ cells, about $3.0\times10^6$ to about $6.0\times10^6$ cells, about $4.0\times10^6$ to about $5.0\times10^6$ cells, about $4.0\times10^6$ to about $6.0\times10^6$ cells, or about $5.0\times10^6$ to about $6.0\times10^6$ cells, prior to expansion in step (c).

In certain embodiments, the sub-population of transfected host cells contains greater than $6.0\times10^6$ cells prior to expansion in step (c). For example, in certain embodiments, the sub-population of transfected host cells comprises about $7.0\times10^6$ cells, about $8.0\times10^6$ cells, about $9.0\times10^6$ cells, or about $10.0\times10^6$ cells, prior to expansion in step (c).

In certain embodiments, the expanding in step (c) is for between 4-31 days. For example, in various embodiments, the expanding is for 4, 5, 6, 7, 8, 9, 10, 11, 12, 13, 14, 15, 16, 17, 18, 19, 20, 21, 22, 23, 24, 25, 26, 27, 28, 29, 30, or 31 days.

In certain embodiments, a first of the one or more vectors encodes the mRNA encoding the target polypeptide, and a second of the one or more vectors encodes the mRNA encoding the selectable polypeptide. Where the one or more vectors encoding the mRNA encoding the target polypeptide and the mRNA encoding the selectable polypeptide are separate vectors, in certain embodiments the vectors are independently selected from plasmids, viruses, phage, transposons, and minichromosomes.

In certain embodiments, the mRNA encoding the target polypeptide and the mRNA encoding the selectable polypeptide are both encoded on one vector. In accordance with these embodiments, a single vector encodes a polycistronic mRNA encoding both the target polypeptide and the selectable polypeptide. Also in accordance with these embodiments, in certain embodiments the mRNA encoding the selectable polypeptide can be upstream (i.e., 5') of the mRNA encoding the target polypeptide. Alternatively, in certain embodiments the mRNA encoding the target polypeptide can be upstream (i.e., 5') of the mRNA encoding the selectable polypeptide.

Thus in certain embodiments, the target polypeptide and the selectable polypeptide are encoded by a single multicistronic mRNA. In certain embodiments, the multicistronic mRNA comprises a first open reading frame (ORF) that encodes the selectable polypeptide and a second ORF that encodes the target polypeptide, wherein the first ORF is 5' to the second ORF.

In certain embodiments, the first ORF has a non-AUG start codon. In certain embodiments, the non-AUG start codon is a UUG, GUG, or CUG in a Kozak consensus sequence. A non-AUG start codon can be installed using standard molecular biology techniques such as are well known in the art.

In certain embodiments, the second ORF has an AUG start codon.

In certain embodiments, the first ORF has a non-AUG start codon, and the second ORF has an AUG start codon.

In certain embodiments, the ORF that encodes the selectable polypeptide is devoid of any AUG sequences. AUG sequences can be converted to other triplet sequences, other than stop codons, using standard molecular biology techniques such as are well known in the art; for example, and without limitation, AUG sequences can be converted independently to CUG (L), GUG (V), UUG (L), AAG (K), ACG (T), AGG (R), AUA (I), AUC (I), AUU (I), GCA (A), GCC (A), GCG (A), or GCU (A).

In certain embodiments, the target polypeptide and the selectable polypeptide form a fusion protein. In certain embodiments, the fusion protein is membrane-bound. When the fusion protein is membrane-bound, in certain embodiments the selectable polypeptide is present in a detectable form, i.e., the target polypeptide portion of the fusion protein does not prohibit detection of the selectable polypeptide portion of the fusion protein. Also when the fusion protein is membrane-bound, in certain embodiments the target polypeptide is present in a functional form, i.e., the selectable polypeptide portion of the fusion protein does not prohibit function of the target polypeptide portion of the fusion protein. In certain embodiments, the fusion protein is released from the host cell as a soluble protein. In certain embodiments, the fusion protein is expressed as a surface protein but can be cleaved to release the target polypeptide in a soluble, functional form.

In certain embodiments, the target polypeptide is a therapeutic agent, e.g., an antibody, an antigen-binding fragment of an antibody, an Fc fusion protein, a hormone, or an enzyme. Polypeptide hormones include, without limitation, adrenocorticotropic hormone (ACTH), antidiuretic hormone (vasopressin), atrial natriuretic peptide (ANP), cholecystokinin, follicle stimulating hormone (FSH), gastrin, glucagon, growth hormone, insulin, leptin, leuteinizing hormone (LH), oxytocin, prolactin, somatostatin, and thyroid stimulating hormone (TSH). Enzymes include, without limitation, acid alpha-glucosidase, adenosine deaminase, alpha-galactosidase, alpha-L-iduronidase, arylsulfatase B, beta-galactosidase, beta-glucuronidase, galactose-6-sulfate sulfatase, glucocerebrosidase, heparan sulfamidase, heparan-alpha-glucosaminide N-acetyltransferase, hyaluronidase, iduronate-2-sulfatase, N-acetylgalactosamine-4-sulfatase, N-acetylglucosamine 6-sulfatase, and N-acetylglucosaminidase.

In some embodiments, the target polypeptide is a secreted protein.

In certain embodiments, the host cells are mammalian cells. In certain embodiments, the host cells are selected from the group consisting of CHO cells, BHK-21 cells, NIH/3T3 cells, HEK293 cells, HeLa cells, SP2/0 cells, NSO cells, C127 cells, COS cells, Vero cells, and U937 cells. All of these cells (cell lines) are commercially available from sources such as American Type Culture Collection (ATCC, Manassas, Va.). In certain embodiments, the host cells are selected from the group consisting of CHO cells, HEK293 cells, and HeLa cells.

An aspect of the invention is a clonal population of transfected host cells that express a selectable polypeptide and a target polypeptide obtainable by the method the invention. In certain embodiments, the clonal population of transfected host cells expresses a FACS-selectable polypeptide and a target polypeptide obtainable by the method the invention.

In certain embodiments, the clonal population yields a 2- to 30-fold improvement in production of the target polypeptide compared to that of a stable pool of transfected but uncloned host cells obtained at step (c).

For example, in some embodiments, the clonal population yields a 2- to 30-fold, 3- to 30-fold, 5- to 30-fold, 10- to 30-fold, 15- to 30-fold, 20- to 30-fold, 25- to 30-fold, 2- to 25-fold, 3- to 25-fold, 5- to 25-fold, 10- to 25-fold, 15- to 25-fold, 20- to 25-fold, 2- to 20-fold, 3- to 20-fold, 5- to 20-fold, 10- to 20-fold, 15- to 20-fold, 2- to 15-fold, 3- to 15-fold, 5- to 15-fold, 10- to 15-fold, 2- to 10-fold, 3- to 10-fold, 5- to 10-fold, 2- to 5-fold, 3- to 5-fold, or 2- to 3-fold improvement in production of the target polypeptide compared to that of a stable pool of transfected but uncloned host cells obtained at step (c). In certain embodiments, the clonal population yields a greater than 30-fold improvement in production of the target polypeptide compared to that of a stable pool of transfected but uncloned host cells obtained at step (c). For example, in certain embodiments, the clonal population yields an up to 40-fold, up to 50-fold, up to 60-fold, up to 70-fold, up to 80-fold, up to 90-fold, or up to 100-fold improvement in production of the target polypeptide compared to a stable pool of transfected but uncloned host cells obtained at step (c).

III. Producer Cells and Methods of Production Thereof

In some embodiments a heterogeneous population of producer cells is provided. The heterogeneous population of producer cells can be produced using any method known in the art or described herein. In some embodiments of any one of the methods provided, the heterogeneous population of producer cells is produced by transfecting cells with a vector that encodes the multicistronic mRNA and subjecting the transfected cells to less than or equal to one round of medium-based selection to select cells expressing varying levels (e.g., a variation of at least 10-, 100-, 1,000-, or 10,000-fold) of the multicistronic mRNA. In some embodiments, the vector further contains a drug-selectable marker, e.g., a dihydrofolate reductase (DHFR) gene, and the medium-based selection is methotrexate (MTX, e.g., 1 nM-100 nM MTX), nucleotide-deficient medium, or a combination thereof. In some embodiments, the vector further contains a glutamine synthetase (GS) gene and the medium-based selection is methionine sulphoximine (MSX, e.g., 25-100 µM MSX). In some embodiments, the vector lacks a drug-selectable marker, e.g., lacks a DHFR gene or GS gene.

In some embodiments, FACS is used to select cells expressing varying levels of the multicistronic mRNA, e.g., by using the FACS selectable polypeptide level to select the cells.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

EXAMPLES

The present invention is further illustrated by the following examples which should not be construed as further limiting.

Figure 1B:
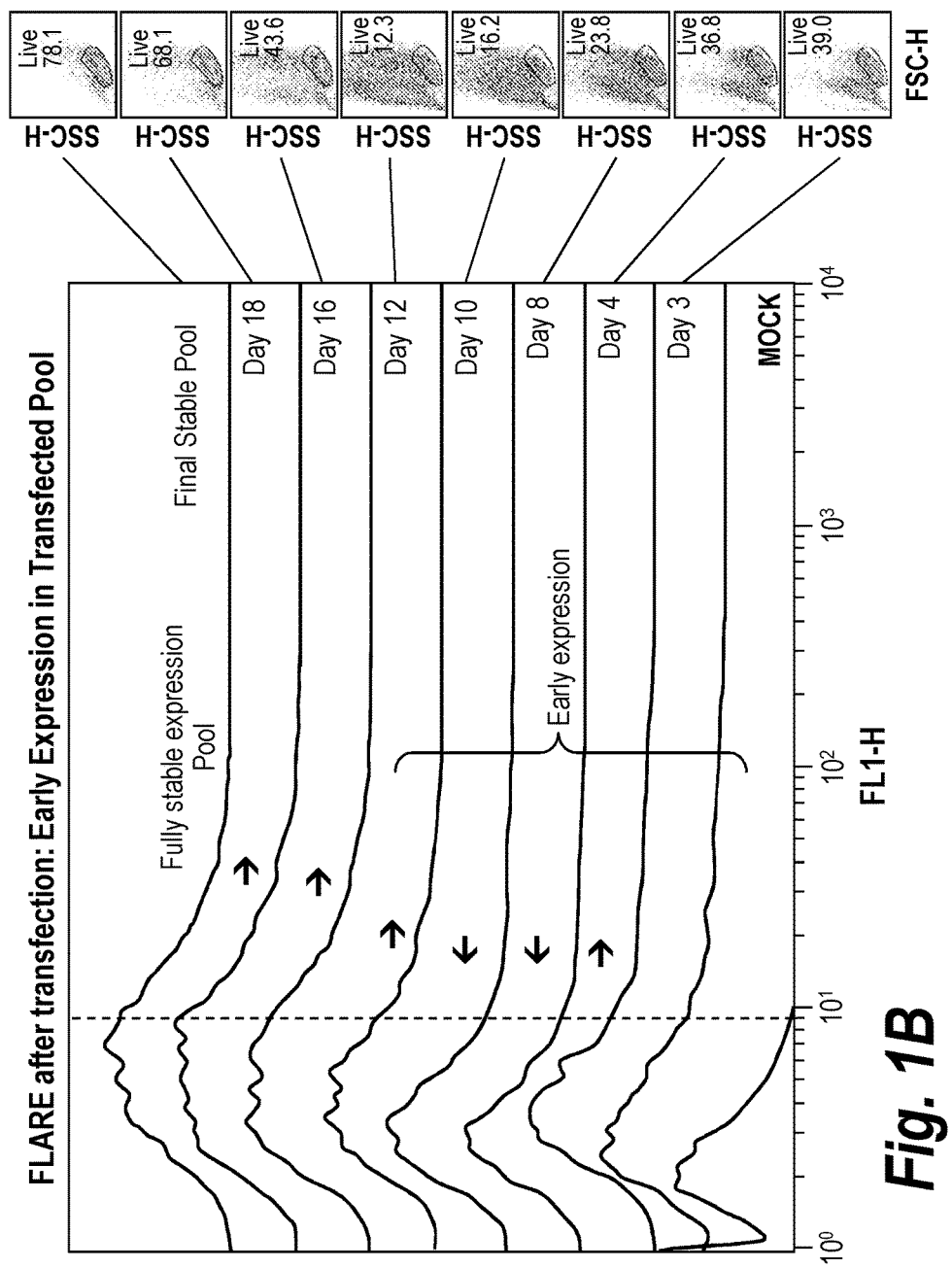
FIG. 1B is a diagram showing reporter expression of a transfected population of cells from day 3 to 21 in a nucleotide-deficient selection process (compared to mock transfected population). Transfected cells exhibited an apparent early expression shortly after transfection (e.g., day 3-4) and then transitioned to stable expression upon completion of selection (day 18-21).

Example 1: Sorting for Early Post-transfection Isolation of Cells (EPIC)—Proof of Concept This example demonstrates the feasibility of a method of sorting to target an unselected transfected early-expressing population for bulk enrichment prior to selection. This method of sorting is called "short sorting" or "EPIC" (Early Post-transfection Isolation of Cells) and is designed to sort-isolate, or bulk enrich, early reporter expression shortly after transfection. EPIC may significantly reduce selection timelines and/or improve productivity of the resulting heterogeneous population. Experiments have been performed to investigate the reporter expression profile of a transfected population throughout the course of a nucleotide-deficient selection process. FIG. 1A depicts a general scheme for EPIC. FIG. 1B shows the early expression of the reporter gene during the nucleotide-deficient selection process. These offset histograms demonstrate that early expression (e.g. day 3-4) is positive and sortable; making isolating a sub-population of transfected cells for an EPIC process feasible.

As shown in FIG. 1A, EPIC can be executed by transfecting a population and allowing early expression to develop, which can be targeted for isolation using flow cytometry or other means of cell sorting. These sort-isolated early-expression sub-populations can then be placed in a selection media to establish a stable expression pool. Isolation of these post-transfection early expression sub-populations prior to selection yields improved productivity over standard transfection/selection methodologies alone (e.g., as shown in FIG. 1A).

To demonstrate proof of concept that detected CD52 signal is in fact early CD52 reporter expression, vectors directing expression of both red fluorescent protein (RFP) and CD52 (pGZ729-RFP) or RFP alone (pGZ700-RFP) were constructed and transfected for early expression evaluation. In this system CD52 corresponds to the detectable polypeptide, and RFP corresponds to the target polypeptide.

The pGZ729 vector backbone sequence (including sequence encoding CD52 but not RFP) is shown below, followed by annotations of the sequence.

Sequence of pGZ729 expression vector
(SEQ ID NO: 6):
ggatccgctgtggaatgtgtgtcagttagggtgtggaaagtccccaggct ccccagcaggcagaagtatgcaaagcatgcatctcaattagtcagcaacc aggtgtggaaagtccccaggctccccagcaggcagaagtatgcaaagcat gcatctcaattagtcagcaaccatagtcccgcccctaactccgcccatcc cgcccctaactccgcccagttccgcccattctccgccccatggctgacta atttttttatttatgcagaggccgaggccgcctcggcctctgagctatt ccagaagtagtgaggaggctttttggaggcctaggcttttgcaaaaagc ttggggggggggacagctcagggctgcgatttcgcgccaaacttgacggc aatcctagcgtgaaggctggtaggattttatcccgctgccatcatggtt cgaccattgaactgcatcgtcgccgtgtcccaaaatatggggattggcaa gaacggagacctaccctggcctccgctcaggaacgagttcaagtacttcc aaagaatgaccacaacctcttcagtggaaggtaaacagaatctggtgatt atgggtaggaaaacctggttctccattcctgagaagaatcgacctttaaa ggacagaattaatatagttctcagtagagaactcaaagaaccaccacgag gagctcattttcttgccaaaagtttggatgatgccttaagacttattgaa caaccggaattggcaagtaaagtagacatggtttggatagtcggaggcag ttctgtttaccaggaagccatgaatcaaccaggccacctcagactctttg tgacaaggatcatgcaggaatttgaaagtgacacgttttttcccagaatt gatttggggaaatataaacttctcccagaatacccaggcgtcctctctga ggtccaggaggaaaaaggcatcaagtataagtttgaagtctacgagaaga aagactaacaggaagatgctttcaagttctctgctcccctcctaaagcta tgcattttataagaccatgggacttttgctggctttagatctttgtgaa ggaaccttacttctgtggtgtgacataattggacaaactacctacagaga tttaaagctctaaggtaaatataaaattttaagtgtataatgtgttaaa ctactgattctaattgtttgtgtattttagattccaacctatggaactga tgaatgggagcagtggtggaatgcctttaatgaggaaaacctgttttgct cagaagaaatgccatctagtgatgatgaggctactgctgactctcaacat tctactcctccaaaaaagaagagaaaggtagaagaccccaaggactttcc ttcagaattgctaagttttttgagtcatgctgtgtttagtaatagaactc ttgcttgctttgctatttacaccacaaaggaaaaagctgcactgctatac aagaaaattatggaaaaatattctgtaacctttataagtaggcataacag ttataatcataacatactgttttttcttactccacacaggcatagagtgt ctgctattaataactatgctcaaaaattgtgtacctttagcttttttaatt tgtaaaggggttaataaggaatatttgatgtatagtgccttgactagaga tcataatcagccataccacatttgtagaggttttacttgctttaaaaaac ctcccacacctcccctgaacctgaaacataaaatgaatgcaattgttgt tgttaacttgtttattgcagcttataatggttacaaataaagcaatagca tcacaaatttcacaaataaagcatttttttcactgcattctagttgtggt ttgtccaaactcatcaatgtatcttatcatgtctggatcctctacgccgg acgcatcgtggccggcatcaccggcgccacaggtgcggttgctggcgcct atatcgccgacatcaccgatggggaagatcgggctcgccacttcgggctc atgagcgcttgtttcggcgtgggtatggtggcaggccgtggccgggggac

```
tgttgggcgccatctccttgcatgcaccattccttgcggcggcggtgctc
aacgcctcaacctactactgggctgcttcctaatgcaggagtcgcataa
gggagagcgtcgaccgatgcccttgagagccttcaacccagtcagctcct
tccggtgggcgcggggcatgactatcgtcgccgcacttatgactgtcttc
tttatcatgcaactcgtaggacaggtgccggcagcgctctgggtcatttt
cggcgaggaccgctttcgctggagcgcgacgatgatcggcctgtcgcttg
cggtattcggaatcttgcacgccctcgctcaagccttcgtcactggtccc
gccaccaaacgtttcggcgagaagcaggccattatcgccggcatggcggc
cgacgcgctgggctacgtcttgctggcgttcgcgacgcgaggctggatgg
ccttccccattatgattcttctcgcttccggcggcatcgggatgcccgcg
ttgcaggccatgctgtccaggcaggtagatgacgaccatcagggacagct
tcaaggccagcaaaaggccaggaaccgtaaaaaggccgcgttgctggcgt
ttttccataggctccgccccctgacgagcatcacaaaaatcgacgctca
agtcagaggtggcgaaacccgacaggactataaagataccaggcgtttcc
ccctggaagctccctcgtgcgctctcctgttccgaccctgccgcttaccg
gatacctgtccgcctttctcccttcgggaagcgtggcgctttctcatagc
tcacgctgtaggtatctcagttcggtgtaggtcgttcgctccaagctggg
ctgtgtgcacgaaccccccgttcagcccgaccgctgcgccttatccggta
actatcgtcttgagtccaacccggtaagcacgacttatcgccactggca
gcagccactggtaacaggattagcagagcgaggtatgtaggcggtgctac
agagttcttgaagtggtggcctaactacggctacactagaaggacagtat
ttggtatctgcgctctgctgaagccagttaccttcggaaaaagagttggt
agctcttgatccggcaaacaaaccaccgctggtagcggtggtttttttgt
ttgcaagcagcagattacgcgcagaaaaaaaggatctcaagaagatcctt
tgatcttttctacggggtctgacgctcagtggaacgaaaactcacgttaa
gggattttggtcatgagattatcaaaaaggatcttcacctagatccttt
aaattaaaaatgaagttttaaatcaatctaaagtatatatgagtaaactt
ggtctgacagttaccaatgcttaatcagtgaggcacctatctcagcgatc
tgtctatttcgttcatccatagttgcctgactccccgtcgtgtagataac
tacgatacgggagggcttaccatctggccccagtgctgcaatgataccgc
gagacccacgctcaccggctccagatttatcagcaataaaccagccagcc
ggaagggccgagcgcagaagtggtcctgcaactttatccgcctccatcca
gtctattaattgttgccgggaagctagagtaagtagttcgccagttaata
gtttgcgcaacgttgttgccattgctgcaggcatcgtggtgtcacgctcg
tcgtttggtatggcttcattcagctccggttcccaacgatcaaggcgagt
tacatgatcccccatgttgtgcaaaaaagcggttagctccttcggtcctc
cgatcgttgtcagaagtaagttggccgcagtgttatcactcatggttatg
gcagcactgcataattctcttactgtcatgccatccgtaagatgcttttc
tgtgactggtgagtactcaaccaagtcattctgagaatagtgtatgcggc
gaccgagttgctcttgcccggcgtcaacacgggataataccgcgccacat
agcagaactttaaaagtgctcatcattggaaaacgttcttcggggcgaaa
actctcaaggatcttaccgctgttgagatccagttcgatgtaacccactc
gtgcacccaactgatcttcagcatcttttactttcaccagcgtttctggg
tgagcaaaaacaggaaggcaaaatgccgcaaaaaagggaataagggcgac
acggaaatgttgaatactcatactcttccttttcaatattattgaagca
tttatcagggttattgtctcatgagcggatacatatttgaatgtatttag
aaaaataaacaaataggggttccgcgcacatttccccgaaaagtgccacc
tgacgtctaagaaaccattattatcatgacattaacctataaaaataggc
gtatcacgaggccctttcgtcttcaagaattggggaccaagacagaacca
taagccagtgggatagatcagaaatgttccagaggtgggatggggccaga
gtgcctgcccctttgaaccgtcccagggaccagaggtgacaaagtggcaac
acaggtcctgcctgggaatctggtctgctcctacttagtaaagctgcctg
gtgtcacacaagaggccccccacttattcctgcacccctggtggtaggtgg
cgtcttctcccctgcagccaccaggctcccctgagaacactgccggcagt
cctcattgacaggcagtattcgctctgccccacccccacctgtgaattgc
agggctggcaggtcctcaggcagctggcaaaccgcctgaacaactgagag
atacagggccagggccagggcagtcccgtccccccggaggcagggagggga
cgtgctgggaaagttctctctctcaggcccaggttggtgactgcagaagg
cttctgtcaaatctcttttgtgggaaccacagagtagccctgaacgtggg
ggtgtgcttccagtatactctggggtcacccttttccatactggaggcctc
tgcaacttcaaaatgctctgctaccaacctagcacaaggaagttggtcca
gcctcccacgcagggccactgctgcagtccatatatggactaagccttc
cttggtttcaacacctacactcactgagcccctactatgtgtatgcagag
ccgagacaggccctgagcatctcatctgaagcacccttcttgcctaaatt
cagttttctgtcactttctcccaggaggtgtgtgtccctctaagctaagc
cagggggtccctcaccccctgccccactccatccctagtgtaggtatcagc
tgaagagcttcctgagcagaacactcttgggtgctgacattttgataaat
aggcccatgtttaggagagcagggtccgggggcgggagatcttctctgg
tggattgagggctccaagaactactctttgagcacgctgcccctcccaga
gtccccacagcctccagatggactagaacacagttcggctgtggctgcac
ataactaacagaggatagatggtgggtcccagcccaacagtgcctggcaa
tcacccagagccaccagctaacggccttggcttagttttttgcctgggtg
tgatcaggcagccctccaaaactgcccggactccatgacaagttttgctt
gttctatagagcacagttcctttctaggtctgggcaagggacatcggga
gacatcttcctgcaacagctccagtcactggaccaccaggctcgccctgt
ctttggtgtgtggccctgagtctcctaagtgcccaaacctgtgaagacc
cctccaaccacagttttgcttctaaattgtaccccaacacacctagcaaa
ttgaaaccccaccagaagtcccccagatctggctttccggctattgctgg
caaggggagtgactcccggcccattcaatccaggccccgcgtgttcctc
aaacaagaagccacgtaaacataaaccgagcctccatgctgaccccttgcc
catcgaggtactcaatgttcacgtgatatccacacccagagggtcctggg
```

-continued

```
gtgggtgcatgagcccagaatgcaggcttgataaccgagaccctgaatc gggcagtgtccacaagggcggaggccagtcatgcatgttcgggcctatgg ggccagcacccaacgccaaaactctccatcctcttcctcaatctcgcttt ctctctctctctctttttttttttttattttttttttttgcaaaaggagg ggagaggggggtaaaaaaatgctgcactgtgcggctaggccggtgagtgag cggcgcggagccaatcagcgctcgccgttccgaaagttgccttttatggc tcgagtggccgctgtggcgtcctataaaaccggcggcgcaacgcgcagc cactgtcgagtccgcgtccaccgcgagcacaggcctttcgcagctcttt cttcgccgctccacacccgccaccaggtaagcagggacaacaggcccagc cggccacagccctcccgtgggcagtgaccgcgctgcagggtcgcggggga cactcggcgcggacaccggggaaggctggagggtggtgccgggccgcgga gcggacactttcagatccaactttcagtccagggtgtagaccctttacag ccgcattgccacggtgtagacaccggtggaccccgctctggctcagagcac gcggcttgggggaacccattagggtcgcagtgtgggcgctatgagagccg atgcagctttcgggtgttgaaccgtatctgcccaccttgggggaggaca caaggtcgggagccaaacgccacgatcatgccttggtggcccatgggtct ttgtctaaaccggtttgcccatttggcttgccgggcgggcgggcgcggcg ggccggctcggccgggtgggggctgggttgccactgcgcttgcgcgctc tatggctgggtattgggcgcgtgcacgctggggagggagcccttcctct tccccctctcccaagttaaacttgcgcgtgcgtattgagacttggagcgc ggccaccgggggttgggcgagggcggggccgttgtccggaagggggcgggt cgcagcggcttcggggcgcctgctcgcgcttcctgctgggtgtggtcgcc tcccgcgcgcgcactagccgcccgccggcggggcgaaggcggggcttgcg cccgtttggggaggggggcggaggcctggcttcctgccgtggggccgcctc cggaccagcgtttgcctcttatggtaataacgcggccggcctgggcttcc tttgtcccctgagtttgggcgcgcgcccctggcggcccgaggccgcggc ttgccggaagtgggcagggcggcagcggctgcgcctagtggcccgctagt gaccgcgaccctcttttgtgccctgatatagttcgccggatcctaccgcg gtagcggccgcgccaccttggagcgcttcctcttcctcctactcaccatc agcctcctcgtttggtacaaatacaaaccggactctccggacaaaacga caccagccaaaccagcagccctcagcatccagcaacataagcggaggca ttttccttttcttcgtcgccaacgccataatccacctcttctgcttcagt tgaaggccggccaatacgtaggcgcgccattgagtgagtgatttggcgcg ccaagatatcacacccgggattaattaaaggtacctacgcgtagaattcc acgtagtggtttaaactctagatactcgagggatctggatcataatcagc cataccacatttgtagaggttttacttgctttaaaaaacctcccacacct cccctgaacctgaaacataaaatgaatgcaattgttgttgttaacttgt ttattgcagcttataatggttacaaataaagcaatagcatcacaaatttc acaaataaagcatttttttcactgcattctagttgtggtttgtccaaact catcaatgtatcttatcatgtct
```

Figure 2:
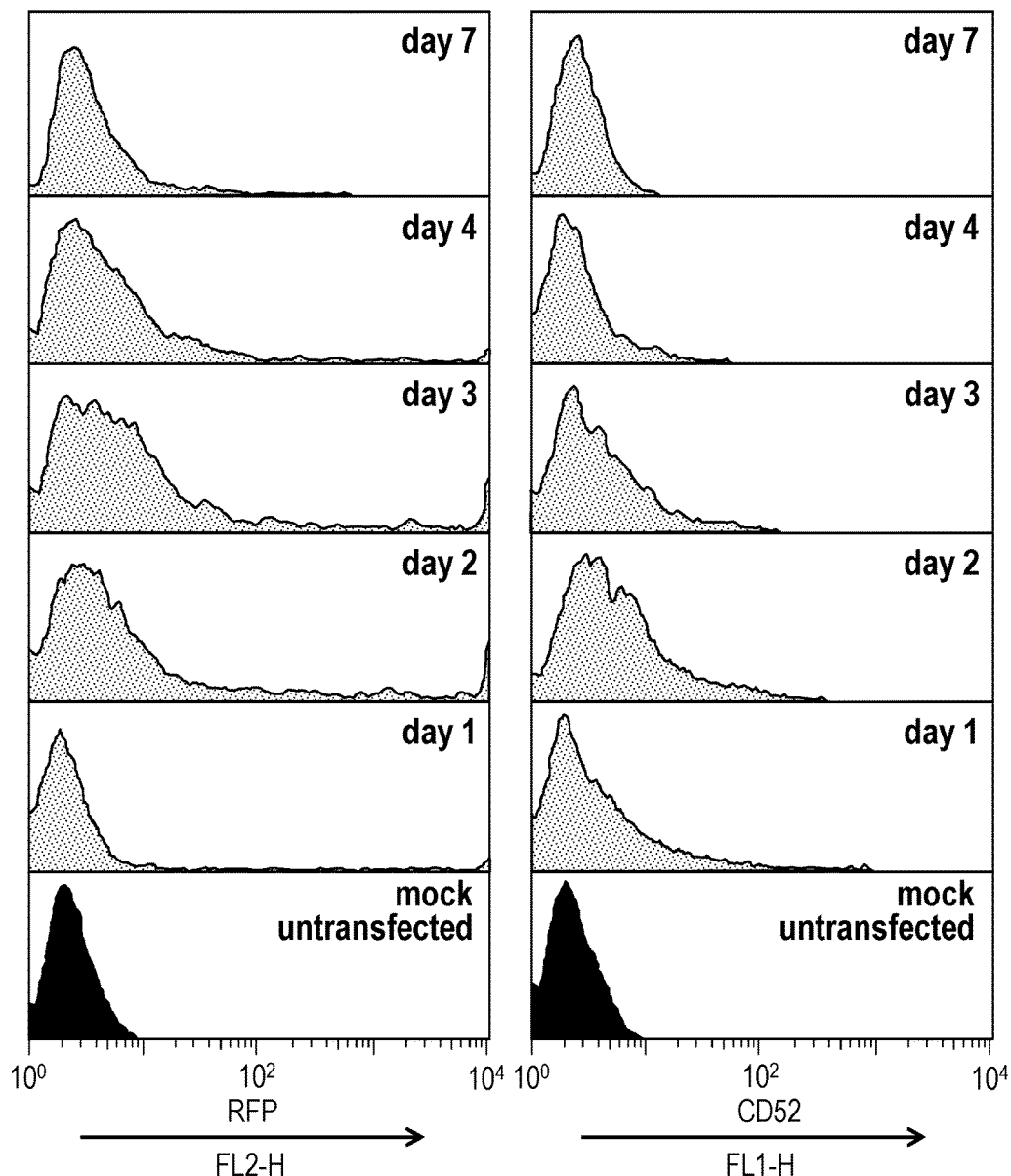
FIG. 2 is a series of FACS histogram offsets depicting the early expression of both red fluorescent protein (RFP) and cell surface reporter CD52 expression from the same vector (pGZ729-RFP). No selection pressure was applied to the transfected cells. Peak early expression for RFP and CD52 occurs between days 2 and 3.
Figure 3:
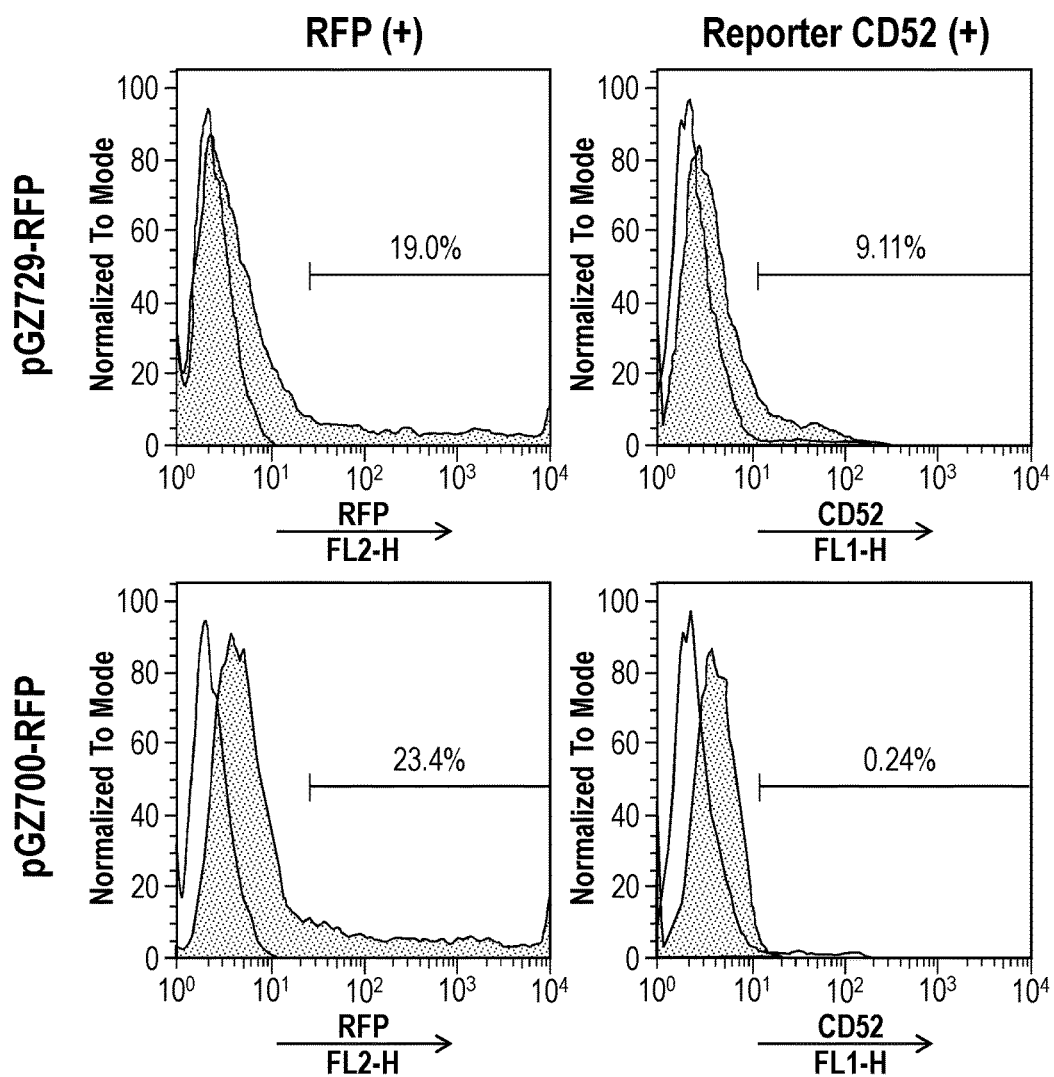
FIG. 3 is a series of FACS histogram offsets depicting the day 3 early expression of RFP and CD52 in cells transfected with pGZ729-RFP (encoding both selectable polypeptide CD52 and target polypeptide RFP) or pGZ700-RFP (encoding only target polypeptide RFP).

Elements of pGZ729 Expression Vector (and Nucleotide Locations):

Nucleotides 1-325—SV40 early promoter (for DHFR transcription)
Nucleotides 347-1089—Dihydrofolate reductase (DHFR) open reading frame
Nucleotides 1090-1934—SV40 early intron and polyA
Nucleotides 2684-3366—E. coli ColE1 origin
Nucleotides 3464-4123—Ampicillin resistance gene
Nucleotides 4528-7539—Hamster β-actin promoter (for transcription of gene of interest)
Nucleotides 7568-7753—CD52 open reading frame (containing TTG start codon)
Nucleotides 7781-7791—Stop codons in each of 3 reading frames
Nucleotides 7813-7872—Multiple cloning site (for insertion of target polypeptide with ATG start codon)
Nucleotides 7882-8123—SV40 early polyA As shown in FIG. 2, CHO cells transfected with pGZ729-RFP produced early expression of both CD52 and RFP that peaked around days 2 and 3, with signal deteriorating out to day 7 post-transfection. Therefore, EPIC targeting on or near days 2-3 is suitable for isolation of early-expressing sub-populations of transfected host cells. In order to demonstrate that these relatively low degree of fluorescence intensity signals were in fact CD52 expression, CHO cells transfected with either pGZ729-RFP or pGZ700-RFP were analyzed for RFP and CD52 expression. As shown in FIG. 3, both CHO cells transfected with pGZ729-RFP and CHO cells transfected with pGZ700-RFP robustly expressed RFP (top left and bottom left, respectively), whereas while CHO cells transfected with pGZ729-RFP had modest expression of CD52 (top right), CHO cells transfected with pGZ700-RFP expressed essentially no detectable CD52 (bottom right). These findings support the notion that these relatively low degree of fluorescence intensitysignals were in fact CD52 expression from the alternate start expression cassette, suitable as a target for sorting isolation (EPIC).

Figure 4:
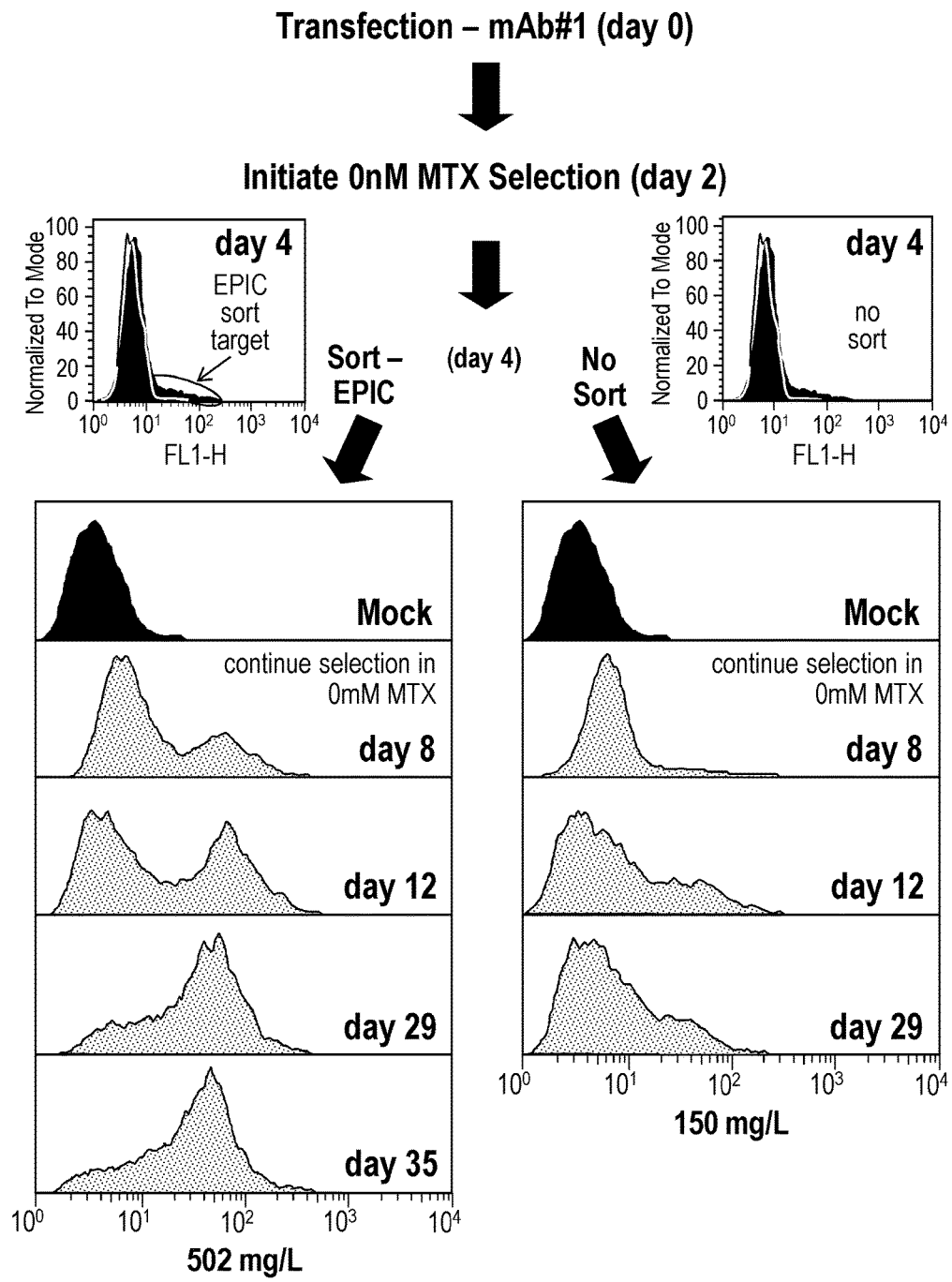
FIG. 4 is a schematic showing both the methodology of EPIC to generate a sub-population of cells for selection shortly after transfection and the beneficial effects to both the reporter expression and monoclonal antibody (mAb) titers upon isolation/expansion of the sort-enriched population. Mock refers to mock transfection.

Example 2: Sorting for Early Post-transfection Isolation of Cells (EPIC)—Producer Cell Pool Generation EPIC was initially attempted using mAb#1 in which CHO cells were transfected and given 2 days to recover, after which 0 nM MTX selection was initiated to establish early expression. Four days after transfection, early expression of CD52 cell surface reporter was targeted for sort isolation (EPIC). Sorting targeted only positive expression which was collected as a bulk enriched population of about 1 million cells which was then allowed to continue selection in nucleotide-deficient media (0 nM MTX). As a control, a non-sorted transfection was allowed to continue selection via standard selection procedure. As shown in FIG. 4, by day 8 sorting for EPIC yielded a slightly enriched population as seen by CD52 reporter expression as compared to standard selection. As selection of both populations continued, however, this small EPIC sub-population became more prominent over time. In fact, the CD52-negative sub-population was all but eliminated upon selection completion. Comparatively, the standard selection method demonstrated a slight improvement in CD52 reporter expression which is historically typical. Sorting for EPIC, or isolating early expression, yielded a sub-population of positive expression that had a preferential survivability over the less expressive cells, which in turn yielded a more productive stable pool.

Figure 5:
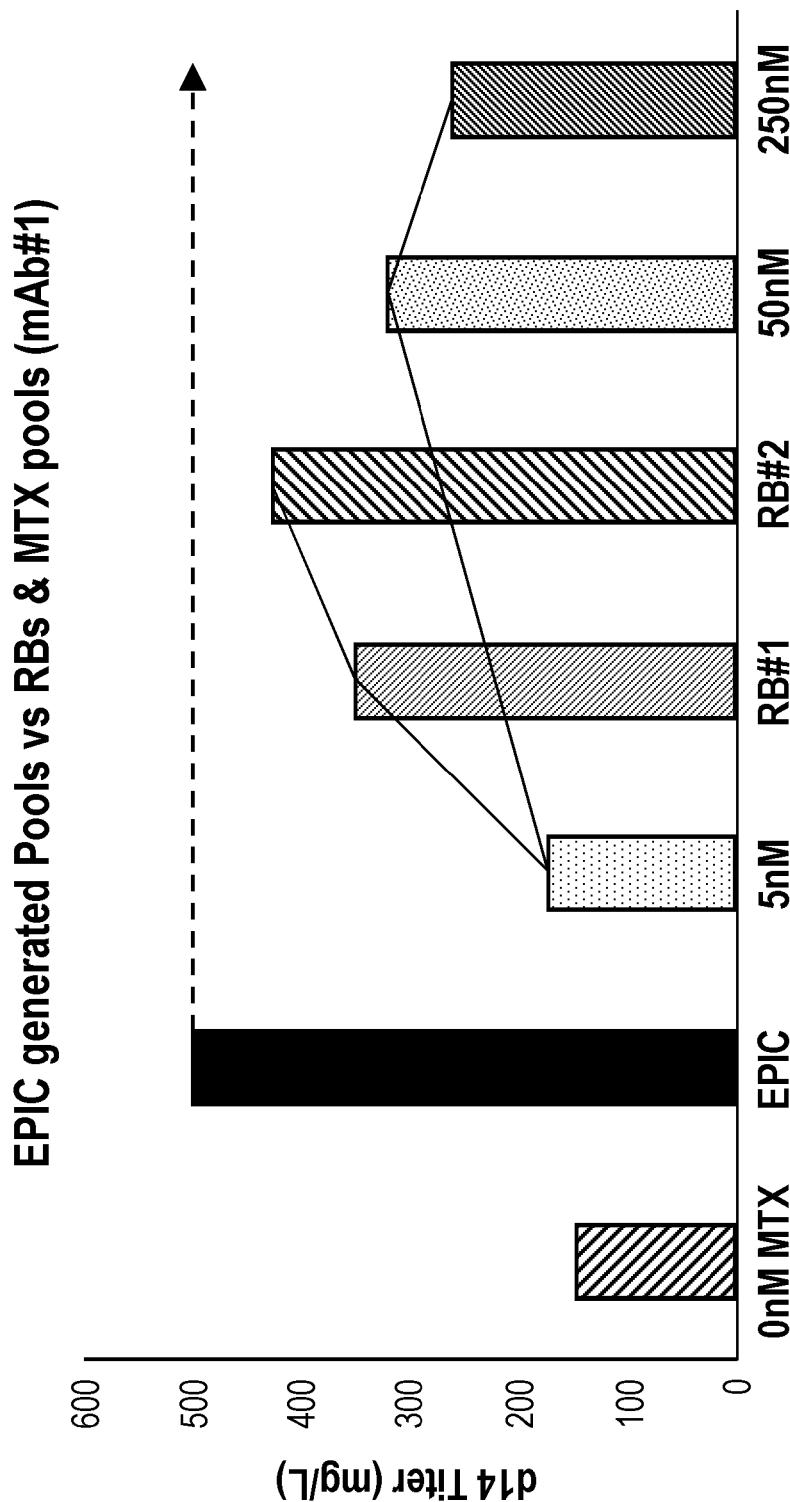
FIG. 5 is a graph depicting day 14 unfed batch titers for EPIC-generated pools as compared to traditional MTX methodologies.

The EPIC and standard selected pools were both used to establish unfed batch cultures to determine mAb#1 titers. As shown in FIGS. 4 and 5, the EPIC-generated pool yielded a titer of 502 mg/L, far outpacing any pools generated by MTX amplification, again using no MTX throughout the processes. Comparatively, the pool generated by standard selection yielded a titer of 150 mg/L, which was 3-fold lower than that of the EPIC-generated pool.

While these initial sorts targeting EPIC took 35 days (transfection/sort/isolation) to achieve completion to a stable pool, this was directly related to the small number of sorted cells collected (1 million) which then had to endure both the expansion and selection to a stable population. Such timelines could be greatly reduced by either simply collecting more cells and/or targeting a purer sort. Many of the cells sorted had high levels of impurities (cells with little to no expression) and had to be selected (killed) out, prolonging the selection/expansion times.

Figure 6:
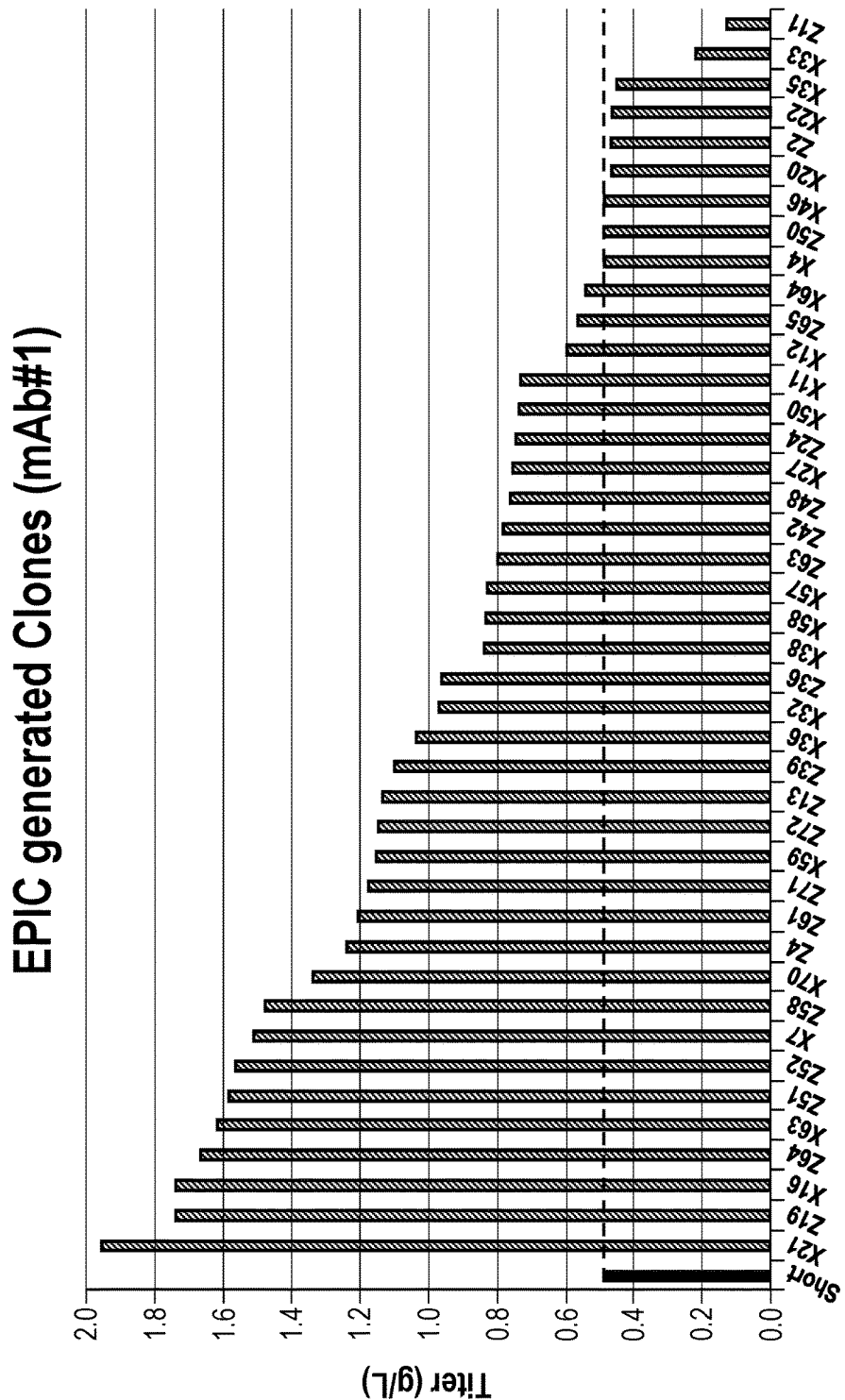
FIG. 6 is a graph depicting day 14 unfed batch titers from EPIC-generated clones which achieved top expression ranging from 1.5-2.0 g/L. Leftmost bar (0.5 g/L) represents titer for EPIC-sorted pool prior to cloning. All other vertical bars represent titers for individual clones.
Figure 7:
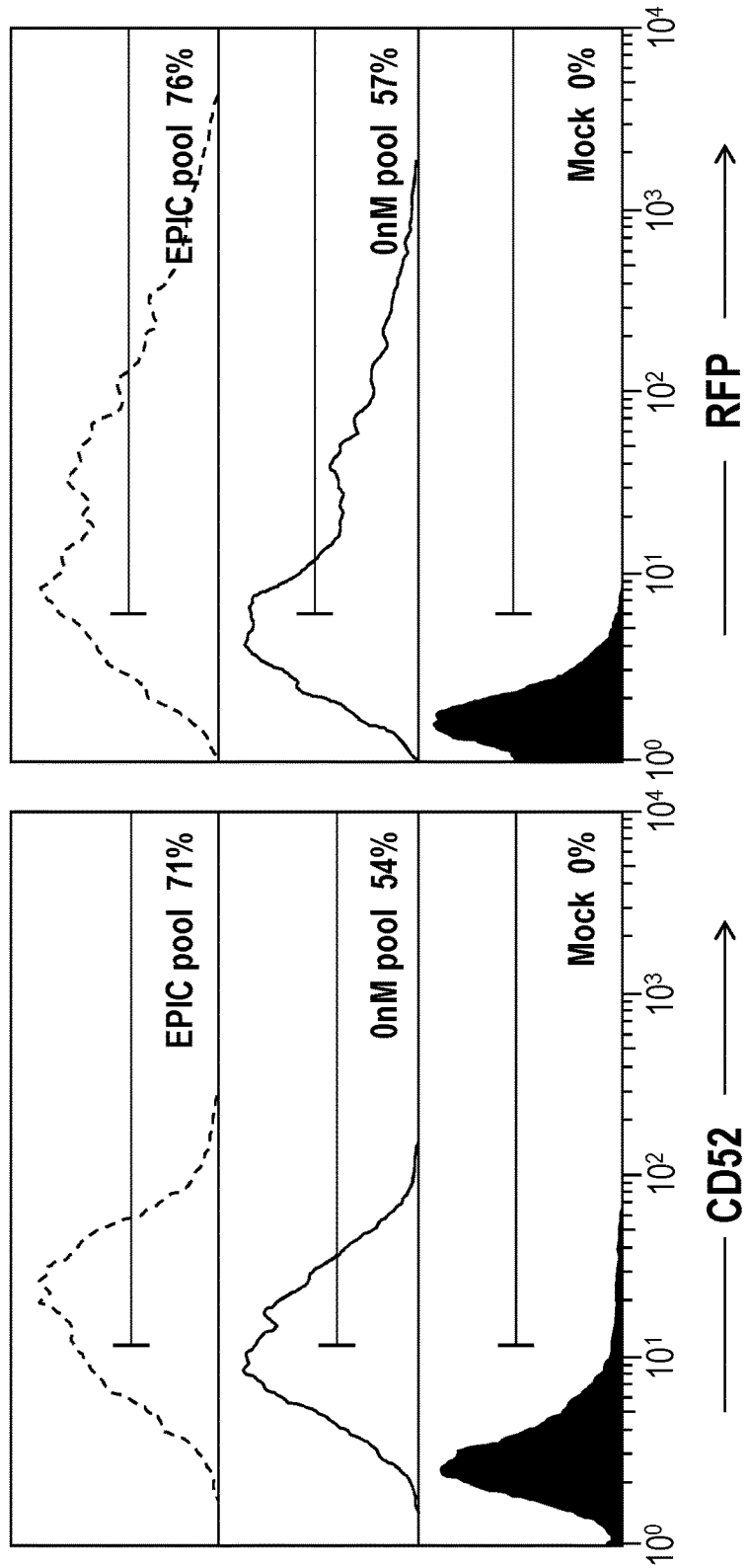
FIG. 7 is a series of histogram offsets depicting the comparative benefit of EPIC targeting to generate stable pools transfected with pGZ729-RFP. EPIC was used to target early RFP expression at day 2 which yielded a stable pool with improved RFP (and CD52 reporter expression) as compared to traditional transfection/selection methodologies (0 nM MTX).

Example 3: Sorting for Early Post-transfection Isolation of Cells (EPIC)—Clone Generation The EPIC-generated pool of Example 2 was next used to generate clones using FLARE as previously described (see, e.g., Cairns, V. et al. (2011) Utilization of Non-AUG Initiation Codons in a Flow Cytometric Method for Efficient Selection of Recombinant Cell Lines. *Biotechnol Bioeng* 108(11):2611-2622). Briefly, FLARE was used to isolate and single cell plate the top 3-5% of reporter-expressing cells from each pool using FACS. Expanded clones were then screened (taking top 30% positive expressers), again using FLARE, to identify only the top tier clones to expand for target polypeptide titer evaluation. As shown in FIG. 6, top expressing EPIC-generated clones achieved similar titers to those of best clones from traditional methods, e.g., using MTX-amplified pools (near 2.0 g/L). Results demonstrated that using EPIC to isolate early expression populations prior to selection is a viable alternative to traditional transfection and selection methodologies. EPIC offers a MTX-independent methodology to achieve clone titers similar to those from traditional MTX methodologies, resulting in potentially more robust and stable clones. Alternatively, EPIC is also amenable to MTX introduction during selection/expansion of EPIC-generated sub-populations, with the potential to drive even higher expression in these enriched populations.

What is claimed is:

1. A method of producing a population of producer cells expressing a target polypeptide, the method comprising:
   (a) transfecting host cells with one or more vectors that encode one or more mRNAs, wherein the one or more mRNAs encode a selectable polypeptide and the target polypeptide, wherein the mRNA encoding the target polypeptide and the mRNA encoding the selectable polypeptide are both encoded on one vector;
   (b) isolating from the transfected host cells, within 2 to 5 days of transfection, a sub-population of early-expressing transfected host cells which express the selectable polypeptide, wherein the isolating employs magnetic activated cell sorting (MACS) or fluorescence activated cell sorting (FACS) on the selectable polypeptide; and
   (c) expanding the isolated sub-population of early-expressing transfected host cells, thereby producing a population of producer cells expressing the target polypeptide,
   wherein the population of producer cells expresses an enhanced level of the target polypeptide compared to an unselected population of the transfected host cells, and
   wherein steps (b) and (c) are each performed in drug-selection-free medium.

2. The method of claim 1, further comprising isolating the target polypeptide from the population of producer cells.

3. The method of claim 1, further comprising isolating one or more single transfected host cells from the population of producer cells expressing the target polypeptide and culturing the one or more single transfected host cells to produce clonal populations of the one or more single transfected host cells.

4. The method of claim 3, wherein at least one of the clonal populations of the one or more single transfected host cells yields a 2- to 30-fold improvement in production of the target polypeptide compared to that of a stable pool of transfected but uncloned host cells derived from the population of producer cells expressing the target polypeptide obtained at step (c).

5. The method of claim 1, wherein the transfected host cells subject to selection in (b) contains at least $80\text{-}120\times10^6$ cells.

6. The method of claim 1, wherein the isolating in step (b) is performed between two and four days after transfection.

7. The method of claim 1, wherein the sub-population of transfected host cells contains $0.5\text{-}6.0\times10^6$ cells prior to expansion in step (c).

8. The method of claim 1, wherein the expanding in step (c) is for between 4-31 days.

9. The method of claim 1, wherein the selectable polypeptide is a FACS selectable polypeptide and the isolating in step (b) employs FACS.

10. The method of claim 1, wherein the target polypeptide and the selectable polypeptide form a fusion polypeptide.

11. The method of claim 1, wherein the target polypeptide and the selectable polypeptide are encoded by a single multicistronic mRNA.

12. The method of claim 11, wherein the multicistronic mRNA comprises a first open reading frame (ORF) that encodes the selectable polypeptide and a second ORF that encodes the target polypeptide, wherein the first ORF is 5' to the second ORF.

13. The method of claim 12, wherein the first ORF has a non-AUG start codon.

14. The method of claim 12, wherein the second ORF has an AUG start codon.

15. The method of claim 12, wherein the ORF that encodes the selectable polypeptide is devoid of any AUG sequences.

* * * * *